US008257593B2

(12) United States Patent
Leonard et al.

(10) Patent No.: US 8,257,593 B2
(45) Date of Patent: *Sep. 4, 2012

(54) SYSTEMS AND METHODS OF MICROFLUIDIC MEMBRANELESS EXCHANGE USING FILTRATION OF EXTRACTION OUTLET STREAMS

(75) Inventors: Edward F. Leonard, Bronxville, NY (US); Alan C. West, Tenafly, NJ (US); Christian Paul Aucoin, New York, NY (US); Edgar E. Nanne, Bronx, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/332,040

(22) Filed: Dec. 20, 2011

(65) Prior Publication Data

US 2012/0103901 A1      May 3, 2012

Related U.S. Application Data

(60) Continuation of application No. 12/759,157, filed on Apr. 13, 2010, now Pat. No. 8,097,153, which is a division of application No. 11/814,117, filed as application No. PCT/US2007/069414 on May 22, 2007, now Pat. No. 7,727,399.

(51) Int. Cl.
*B01D 61/38*     (2006.01)
*B01D 61/24*     (2006.01)
*B01D 61/14*     (2006.01)
*B01D 11/00*     (2006.01)
*A61M 1/34*      (2006.01)
*A61M 37/00*     (2006.01)

(52) U.S. Cl. ........ 210/643; 210/511; 210/634; 210/644; 210/645; 210/651; 210/767; 210/806; 604/5.01; 604/5.04; 604/6.01; 604/6.02; 604/6.09

(58) Field of Classification Search ............ 210/97, 210/137, 200, 203, 209, 511, 643, 644, 645, 210/646, 647, 649, 650, 651, 634, 767, 806; 604/5.01, 5.04, 6.01, 6.02, 6.09, 6.11
See application file for complete search history.

(56) References Cited

U.S. PATENT DOCUMENTS 2,885,782 A     5/1959     Groves
(Continued)

FOREIGN PATENT DOCUMENTS

DE     20113789     5/2002
(Continued)

OTHER PUBLICATIONS

Abbitt et al., "Rheological Properties of the Blood Influencing Selectin-Mediated Adhesion of Flowing Leukocytes." American Journal of Physiology: Heart and Circulatory Physiology, Jul. 2003, 285(1): pp. H229-H240.

(Continued)

*Primary Examiner* — John Kim
(74) *Attorney, Agent, or Firm* — Miles & Stockbridge, P.C.; Mark A. Catan, Esq.

(57) ABSTRACT

A device, system and method for exchanging components between first and second fluids by direct contact in a microfluidic channel. The fluids flow as thin layers in the channel. One of the fluids is passed through a filter upon exiting the channel and is recycled through a secondary processor which changes the fluid's properties. The recycled fluid is reused for further exchange. The filter excludes blood cells from the recycled fluid and prevents or limits clogging of the filter. The secondary processor removes metabolic waste and water by diafiltration.

8 Claims, 11 Drawing Sheets

U.S. PATENT DOCUMENTS

| | | |
|---|---|---|
| 3,388,803 A | 6/1968 | Scott |
| 3,506,126 A | 4/1970 | Lindsay et al. |
| 3,619,423 A | 11/1971 | Galletti et al. |
| 3,746,175 A | 7/1973 | Markley |
| 3,799,873 A | 3/1974 | Brown |
| 3,884,808 A | 5/1975 | Scott |
| 3,939,069 A | 2/1976 | Granger et al. |
| 3,989,622 A | 11/1976 | Marantz et al. |
| 3,994,799 A | 11/1976 | Yao et al. |
| 4,066,549 A | 1/1978 | Oeser et al. |
| 4,083,786 A | 4/1978 | Tsuda et al. |
| 4,094,775 A | 6/1978 | Mueller |
| 4,137,921 A | 2/1979 | Okuzumi et al. |
| 4,153,554 A | 5/1979 | von der Heide et al. |
| 4,166,800 A | 9/1979 | Fong |
| 4,181,983 A | 1/1980 | Kulkarni |
| 4,212,738 A | 7/1980 | Henne |
| 4,212,742 A | 7/1980 | Solomon et al. |
| 4,243,775 A | 1/1981 | Rosensaft et al. |
| 4,247,393 A | 1/1981 | Wallace |
| 4,267,040 A | 5/1981 | Schal |
| 4,269,708 A | 5/1981 | Bonomini et al. |
| 4,279,249 A | 7/1981 | Vert et al. |
| 4,300,565 A | 11/1981 | Rosensaft et al. |
| 4,321,192 A | 3/1982 | Jain |
| 4,347,234 A | 8/1982 | Wahlig et al. |
| 4,384,975 A | 5/1983 | Fong |
| 4,390,519 A | 6/1983 | Sawyer |
| 4,394,370 A | 7/1983 | Jefferies |
| 4,409,332 A | 10/1983 | Jefferies et al. |
| 4,431,019 A | 2/1984 | Kopp et al. |
| 4,443,333 A | 4/1984 | Mahurkar |
| 4,530,449 A | 7/1985 | Nozawa et al. |
| 4,538,603 A | 9/1985 | Pawelchak et al. |
| 4,539,981 A | 9/1985 | Tunc |
| 4,563,489 A | 1/1986 | Urist |
| 4,568,559 A | 2/1986 | Nuwayser et al. |
| 4,578,384 A | 3/1986 | Hollinger |
| 4,585,797 A | 4/1986 | Cioca |
| 4,596,574 A | 6/1986 | Urist |
| 4,623,588 A | 11/1986 | Nuwayser et al. |
| 4,661,246 A | 4/1987 | Ash |
| 4,663,049 A | 5/1987 | Kolff et al. |
| 4,678,566 A | 7/1987 | Watanabe et al. |
| 4,703,108 A | 10/1987 | Silver et al. |
| 4,741,337 A | 5/1988 | Smith et al. |
| 4,744,365 A | 5/1988 | Kaplan et al. |
| 4,765,899 A | 8/1988 | Wells et al. |
| 4,765,907 A | 8/1988 | Scott |
| 4,795,804 A | 1/1989 | Urist |
| 4,818,542 A | 4/1989 | DeLuca et al. |
| 4,822,278 A | 4/1989 | Oliva et al. |
| 4,837,285 A | 6/1989 | Berg et al. |
| 4,839,130 A | 6/1989 | Kaplan et al. |
| 4,844,854 A | 7/1989 | Kaplan et al. |
| 4,849,340 A | 7/1989 | Oberhardt |
| 4,877,864 A | 10/1989 | Wang et al. |
| 4,889,119 A | 12/1989 | Jamiolkowski et al. |
| 4,897,189 A | 1/1990 | Greenwood et al. |
| 4,898,186 A | 2/1990 | Ikada et al. |
| 4,898,734 A | 2/1990 | Mathiowitz et al. |
| 4,916,193 A | 4/1990 | Tang et al. |
| 4,938,763 A | 7/1990 | Dunn et al. |
| 4,961,707 A | 10/1990 | Magnusson et al. |
| 4,968,422 A | 11/1990 | Runge et al. |
| 4,968,590 A | 11/1990 | Kuberasampath et al. |
| 4,975,527 A | 12/1990 | Koezuka et al. |
| 4,997,570 A | 3/1991 | Polaschegg |
| 5,004,602 A | 4/1991 | Hutchinson |
| 5,007,939 A | 4/1991 | Delcommune et al. |
| 5,011,691 A | 4/1991 | Oppermann et al. |
| 5,011,692 A | 4/1991 | Fujioka et al. |
| 5,013,649 A | 5/1991 | Wang et al. |
| 5,037,639 A | 8/1991 | Tung |
| 5,051,272 A | 9/1991 | Hermes et al. |
| 5,077,049 A | 12/1991 | Dunn et al. |
| 5,080,665 A | 1/1992 | Jarrett et al. |
| 5,081,106 A | 1/1992 | Bentley et al. |
| 5,084,051 A | 1/1992 | Tormala et al. |
| 5,106,748 A | 4/1992 | Wozney et al. |
| 5,108,753 A | 4/1992 | Kuberasampath et al. |
| 5,108,755 A | 4/1992 | Daniels et al. |
| 5,114,932 A | 5/1992 | Runge |
| 5,116,738 A | 5/1992 | Wang et al. |
| 5,128,136 A | 7/1992 | Bentley et al. |
| 5,133,755 A | 7/1992 | Brekke |
| 5,141,905 A | 8/1992 | Rosen et al. |
| 5,143,730 A | 9/1992 | Fues et al. |
| 5,149,691 A | 9/1992 | Rutherford |
| 5,162,430 A | 11/1992 | Rhee et al. |
| 5,166,058 A | 11/1992 | Wang et al. |
| 5,171,217 A | 12/1992 | March et al. |
| 5,185,152 A | 2/1993 | Peyman |
| 5,187,076 A | 2/1993 | Wozney et al. |
| 5,192,741 A | 3/1993 | Orsolini et al. |
| 5,193,688 A | 3/1993 | Giddings |
| 5,197,977 A | 3/1993 | Hoffman, Jr. et al. |
| 5,206,028 A | 4/1993 | Li |
| 5,227,157 A | 7/1993 | McGinity et al. |
| 5,231,169 A | 7/1993 | Constantz et al. |
| 5,250,584 A | 10/1993 | Ikada et al. |
| 5,268,167 A | 12/1993 | Tung |
| 5,268,178 A | 12/1993 | Calhoun et al. |
| 5,271,961 A | 12/1993 | Mathiowitz et al. |
| 5,278,201 A | 1/1994 | Dunn et al. |
| 5,278,202 A | 1/1994 | Dunn et al. |
| 5,281,419 A | 1/1994 | Tuan et al. |
| 5,284,470 A | 2/1994 | Beltz |
| 5,284,559 A | 2/1994 | Lim et al. |
| 5,288,496 A | 2/1994 | Lewis |
| 5,308,623 A | 5/1994 | Fues et al. |
| 5,320,624 A | 6/1994 | Kaplan et al. |
| 5,324,307 A | 6/1994 | Jarrett et al. |
| 5,324,520 A | 6/1994 | Dunn et al. |
| 5,350,580 A | 9/1994 | Muchow et al. |
| 5,360,610 A | 11/1994 | Tice et al. |
| 5,366,508 A | 11/1994 | Brekke |
| 5,366,733 A | 11/1994 | Brizzolara et al. |
| 5,366,734 A | 11/1994 | Hutchinson |
| 5,376,636 A | 12/1994 | Rutherford et al. |
| 5,415,532 A | 5/1995 | Loughnane et al. |
| 5,437,857 A | 8/1995 | Tung |
| 5,460,803 A | 10/1995 | Tung |
| 5,534,244 A | 7/1996 | Tung |
| 5,562,895 A | 10/1996 | Tung |
| 5,577,891 A | 11/1996 | Loughnane et al. |
| 5,656,153 A | 8/1997 | Kameno et al. |
| 5,716,852 A | 2/1998 | Yager et al. |
| 5,725,776 A | 3/1998 | Kenley et al. |
| 5,744,042 A | 4/1998 | Stange et al. |
| 5,753,014 A | 5/1998 | Van Rijn |
| 5,798,042 A | 8/1998 | Chu et al. |
| 5,833,954 A | 11/1998 | Chow et al. |
| 5,855,562 A | 1/1999 | Moore et al. |
| 5,871,360 A | 2/1999 | Kato |
| 5,885,829 A | 3/1999 | Mooney et al. |
| 5,902,336 A | 5/1999 | Mishkin |
| 5,917,322 A | 6/1999 | Gershenfeld et al. |
| 5,932,100 A | 8/1999 | Yager et al. |
| 5,944,684 A | 8/1999 | Roberts et al. |
| 5,948,684 A | 9/1999 | Weigl et al. |
| 5,980,481 A | 11/1999 | Gorsuch |
| 5,984,891 A | 11/1999 | Keilman et al. |
| 5,993,786 A | 11/1999 | Chow et al. |
| 6,000,341 A | 12/1999 | Tung |
| 6,001,897 A | 12/1999 | Dickens |
| 6,056,930 A | 5/2000 | Tung |
| 6,114,408 A | 9/2000 | Dickens |
| 6,117,100 A | 9/2000 | Powers et al. |
| 6,117,122 A | 9/2000 | Din et al. |
| 6,128,764 A | 10/2000 | Gottesman |
| 6,159,739 A | 12/2000 | Weigl et al. |
| 6,187,838 B1 | 2/2001 | Dickens |
| 6,196,992 B1 | 3/2001 | Keilman et al. |
| 6,197,494 B1 | 3/2001 | Oberhardt |
| 6,206,959 B1 | 3/2001 | Dickens |
| 6,210,759 B1 | 4/2001 | Dickens |

| | | |
|---|---|---|
| 6,281,256 B1 | 8/2001 | Harris et al. |
| 6,317,766 B1 | 11/2001 | Grover |
| 6,332,985 B1 | 12/2001 | Sherman et al. |
| 6,398,859 B1 | 6/2002 | Dickens et al. |
| 6,406,631 B1 | 6/2002 | Collins et al. |
| 6,413,498 B1 | 7/2002 | Malmagro |
| 6,432,630 B1 | 8/2002 | Blankenstein |
| 6,459,097 B1 | 10/2002 | Zagoskin |
| 6,472,210 B1 | 10/2002 | Holy et al. |
| 6,488,896 B2 | 12/2002 | Weigl et al. |
| 6,504,172 B2 | 1/2003 | Zagoskin et al. |
| 6,511,814 B1 | 1/2003 | Carpenter |
| 6,527,735 B1 | 3/2003 | Davankov et al. |
| 6,551,842 B1 | 4/2003 | Carpenter |
| 6,561,997 B1 | 5/2003 | Weitzel et al. |
| 6,563,311 B2 | 5/2003 | Zagoskin |
| 6,582,385 B2 | 6/2003 | Burbank et al. |
| 6,585,682 B1 | 7/2003 | Haraldsson et al. |
| 6,602,719 B1 | 8/2003 | Carpenter |
| 6,605,822 B1 | 8/2003 | Blais et al. |
| 6,614,047 B2 | 9/2003 | Tzalenchuk et al. |
| 6,670,630 B2 | 12/2003 | Blais et al. |
| 6,742,661 B1 | 6/2004 | Schulte et al. |
| 6,743,626 B2 | 6/2004 | Baum et al. |
| 6,758,975 B2 | 7/2004 | Peabody et al. |
| 6,784,451 B2 | 8/2004 | Amin et al. |
| 6,793,725 B2 | 9/2004 | Chow et al. |
| 6,796,955 B2 | 9/2004 | O'Mahoney et al. |
| 6,803,599 B2 | 10/2004 | Amin et al. |
| 6,897,468 B2 | 5/2005 | Blais et al. |
| 6,899,915 B2 | 5/2005 | Yelick et al. |
| 6,900,456 B2 | 5/2005 | Blais et al. |
| 6,911,664 B2 | 6/2005 | Il'ichev et al. |
| 6,930,320 B2 | 8/2005 | Blais et al. |
| 7,002,174 B2 | 2/2006 | Il'ichev et al. |
| 7,052,907 B2 | 5/2006 | Shi et al. |
| 7,118,676 B2 | 10/2006 | Mueth et al. |
| 7,150,834 B2 | 12/2006 | Mueth et al. |
| 7,309,232 B2 | 12/2007 | Rutherford et al. |
| 7,309,323 B2 | 12/2007 | Gura et al. |
| 7,351,218 B2 | 4/2008 | Bene |
| 7,641,871 B2 | 1/2010 | Futami et al. |
| 8,097,162 B2 * | 1/2012 | Leonard et al. ............ 210/643 |
| 2001/0048637 A1 | 12/2001 | Weigl et al. |
| 2001/0055546 A1 | 12/2001 | Weigl et al. |
| 2002/0052571 A1 | 5/2002 | Fazio |
| 2002/0090644 A1 | 7/2002 | Weigl et al. |
| 2002/0159920 A1 | 10/2002 | Weigl |
| 2002/0172622 A1 | 11/2002 | Weigl et al. |
| 2003/0034306 A1 | 2/2003 | Schulte et al. |
| 2003/0226806 A1 | 12/2003 | Young et al. |
| 2004/0009096 A1 | 1/2004 | Wellman |
| 2004/0016918 A1 | 1/2004 | Amin et al. |
| 2004/0045891 A1 | 3/2004 | Gilbert et al. |
| 2004/0069708 A1 | 4/2004 | Laurell et al. |
| 2004/0082903 A1 | 4/2004 | Micheli |
| 2004/0225249 A1 | 11/2004 | Leonard et al. |
| 2004/0245102 A1 | 12/2004 | Gilbert et al. |
| 2005/0082210 A1 | 4/2005 | Favre |
| 2005/0101901 A1 | 5/2005 | Gura |
| 2005/0121604 A1 | 6/2005 | Mueth et al. |
| 2005/0178727 A1 | 8/2005 | Takagi et al. |
| 2005/0201903 A1 | 9/2005 | Weigl et al. |
| 2005/0202563 A1 | 9/2005 | Dasgupta et al. |
| 2005/0215936 A1 | 9/2005 | Gorsuch et al. |
| 2005/0247564 A1 | 11/2005 | Volkel et al. |
| 2005/0266582 A1 | 12/2005 | Modlin et al. |
| 2006/0076295 A1 | 4/2006 | Leonard et al. |
| 2007/0026381 A1 | 2/2007 | Huang et al. |
| 2007/0029257 A1 | 2/2007 | Mueth et al. |
| 2007/0054293 A1 | 3/2007 | Liu et al. |
| 2007/0179435 A1 | 8/2007 | Braig et al. |
| 2007/0179436 A1 | 8/2007 | Braig et al. |
| 2008/0009780 A1 | 1/2008 | Leonard et al. |
| 2008/0015487 A1 | 1/2008 | Szamosfalvi et al. |
| 2008/0023399 A1 | 1/2008 | Inglis et al. |
| 2008/0093298 A1 | 4/2008 | Browning et al. |
| 2009/0292234 A1 | 11/2009 | Leonard et al. |
| 2010/0004578 A1 | 1/2010 | Leonard et al. |
| 2011/0062083 A1 | 3/2011 | Leonard et al. |
| 2011/0066097 A1 | 3/2011 | Leonard et al. |

FOREIGN PATENT DOCUMENTS

| | | |
|---|---|---|
| EP | 1622691 | 2/2006 |
| JP | 10-507962 | 8/1998 |
| JP | 2000-512541 | 9/2000 |
| JP | 2001-511520 | 8/2001 |
| JP | 2002-509248 | 3/2002 |
| JP | 2005-103541 | 4/2005 |
| JP | 2006-520246 | 9/2006 |
| JP | 11-508182 | 7/2009 |
| WO | WO 02/36246 | 5/2002 |
| WO | WO 02/45813 | 6/2002 |
| WO | WO 02/62454 | 8/2002 |
| WO | WO 2004/082796 | 9/2004 |

OTHER PUBLICATIONS

Blackshear, P.L., "Two new concepts that might lead to a wearable artificial kidney," Kidney International, Supplement, Jun. 1978, 8:S133-S137.

Giddings, J.C., "Continuous Separation in Split-Flow Thin (Splitt) Cells Potential Applications to Biological Materials." Separation Science and Technology, 1988, 23(8& 9) : pp. 931-943.

Goldsmith et al., "Margination of Leukocytes in Blood Flow Through Small Tubes" Microvascular Research, Mar. 1984, 27(2): pp. 204-222.

Harper, G., "Home Hemodialysis: A Patient's Perspective." Home Hemodialysis International, 1997, 1: pp. 8-11.

Henne et al, "A Wearable Artificial-Kidney," Artificial Organs, 1977, 1(1): p. 126.

Leonard et al., "Dialysis without Membranes: How and Why?," Blood Purification, 2004, 22 (1):pp. 92-100.

Leonard et al., "Membraneless Dialysis—Is it Possible?" Contributions to Nephrology, 2005, 149: pp. 343-353.

Levin et al., "Analytical Splitt Fractionation in the Diffusion Mode Operating as a Dialysis-Like System Devoid of Membrane—Application to Drug-Carrying Liposomes." Analytical Chemistry, 1993, 65(17): pp. 2254-2261.

Neff et al., "A Wearable Artificial Glomerulus," Transactions—American Society for Artificial Internal Organs, 1979, 25: pp. 71-73.

Ronco, C., "Microfluidic, Membrane-Free Dialysis," American Society of Nephrology, Annual Meeting. 2002.

Schmuhl et al., "Si-Supported Mesoporous and Microporous Oxide Interconnects as Electrophoretic Gates for Application in Microfuidic Devices." Analytical Chemistry, Jan. 2005, 77(1): pp. 178-184.

Seo et al., "Improvement of the Wearable Artificial Kidney," International Journal of Artificial Organs, 1981, 5(3): pp. 321.

Singh et al., "Haematocrit Dependence of Cellular Axial Migration and Tubular Pinch Effects in Blood Flow Through Glass Capillaries," Current Science, Feb. 1990, 59(4): pp. 223-226.

Takai et al., "A New Treatment Strategy Using Both Intermittent Short Dialysis and Continuous Ambulatory Hemofiltration," Transactions of the American Society for Artificial Internal Organs, 1991, 37(3):pp. M325-M327.

Takayama et al., "Topographical Micropatterning of Poly(dimethylsiloxane) Using Laminar Flows of Liquids in Capillaries," Advanced Materials, Apr. 2001, 13(8): pp. 570-574.

Vanholder et al., "Pitfalls of Wearable Artificial-Kidney," International Journal of Artificial Organs, 1990, 13(11): pp. 715-719.

* cited by examiner

SYSTEMS AND METHODS OF MICROFLUIDIC MEMBRANELESS EXCHANGE USING FILTRATION OF EXTRACTION OUTLET STREAMS

CROSS-REFERENCE TO RELATED APPLICATIONS

This application is a continuation of U.S. application Ser. No. 12/759,157, filed Apr. 13, 2010, currently pending, which is a divisional of U.S. application Ser. No. 11/814,117, filed Jul. 17, 2007, issued as U.S. Pat. No. 7,727,399 on Jun. 1, 2010, which is a U.S. national stage application of International Application No. PCT/US2007/069414, filed May 22, 2007, now expired, which claims the benefit of U.S. Provisional Application Ser. No. 60/802,471, filed May 22, 2006, all of which are hereby incorporated by reference herein in their entireties.

FIELD OF THE INVENTION

The invention generally relates to component exchange between fluids. More specifically, the invention relates to selective separation of the components of a sample fluid (e.g., blood fluid) by microfluidic membraneless exchange.

BACKGROUND

Extracorporeal processing of blood is known to have varied uses. Such processing can be used, for example, to provide treatment of a disease. To treat end stage renal disease, for example, hemodialysis is the most commonly employed form of extracorporeal processing for this purpose. Extraction of blood components can be used to remove other components for treatment, such as free viral particles and, in the treatment of congestive heart failure, to remove water and a non-selective cohort of electrolytes. Additional uses for extracorporeal processing include extracting blood components useful in treating disease conditions or in research and/or diagnosis. Apheresis of plasma (i.e., plasmapheresis) and thrombocytes, or platelets, is the procedure most commonly employed for this purpose. Although the present specification describes primarily blood processing and issues related thereto, many of the methods described may be used for processing other fluids as well.

Many different extracorporeal blood processing techniques have been developed which seek to separate components from the blood. The component that is to be separated varies depending on the purpose of the process. It will be understood that as used herein, blood, or blood fluid, refers to a fluid having blood components. It is desirable to extract components, such as metabolic products or poisons from the blood fluid. These metabolic products can be small molecules or toxins of larger molecular weight, generally termed "middle molecules."

The most common process utilizes an artificial membrane of substantial area, across which selected blood components are induced to flow. This flow is generally induced by a transmembrane difference in either concentration or pressure, or a combination of the two. Another form of blood processing calls for the separation of components from blood by passing the blood over sorbent particles. In yet other forms of blood processing, blood is directly contacted with an immiscible liquid (e.g., a fluorocarbon liquid), with the desired result being the removal of dissolved carbon dioxide and the provision of oxygen. The usefulness of blood processing techniques employing immiscible liquids is limited, however, because these immiscible liquids generally have limited capacity to accept the blood components that are desirable to extract.

One common example of a therapeutic use for blood processing is for the mitigation of the species and volume imbalances accompanying end-stage renal disease. The population of patients treated in this manner (e.g., through hemodialysis) exceeds 300,000 in the United States and continues to grow, with the cost of basic therapy exceeding $8 billion per year excluding complications. The overwhelming majority of these patients (about 90%), moreover, are treated in dialysis centers, generally in thrice-weekly sessions. While procedures have been, and continue to be, refined, the basic components and methods of the most common treatment, hemodialysis, were largely established in the 1970's. A typical hemodialysis device consists of a bundle of several thousand permeable hollow fibers, each of which is about 25 cm long and about 200 μm in internal diameter. The fibers are perfused externally by dialyzing solution. The device is operated principally in a diffusive mode, but a transmembrane pressure is also applied to induce a convective outflow of water. Upwards of 120 liters per week of patient blood are dialyzed against upwards of 200 liters per week of dialyzing solution, often in three weekly treatments that total seven to nine hours per week. These numbers vary somewhat, and competing technologies exist, but the basic approach just described predominates.

Despite the benefits of therapies (e.g., hemodialysis) using the various forms of blood processing described above, the prolongation of life achieved is complicated by the progression and complexity of the diseases that the therapies are used to treat, and by several problems that are innate to the therapies themselves. Few patients on dialysis are ever completely rehabilitated. Problems arise with blood processing as a result of the contact of blood with the surfaces of artificial membranes, sorbents, or immiscible fluids, as described above. Such contact often induces biochemical reactions in the blood being processed, including the reactions that are responsible for clotting, activation of the complement systems, and irreversible aggregation of blood proteins and cells.

Another problem associated with known blood processing techniques is that the contact of blood with artificial membranes or sorbents can cause the blood-medium interface to become fouled. It is generally known that blood purification procedures (e.g., those related to end-stage renal disease) are optimally conducted in such a manner as to maintain a healthy equilibrium state. In practice it has been recognized that treatment should be performed at a limited rate and in as nearly a continuous fashion as possible to avoid the consequences of rapid changes in the composition of body fluids, such as exhaustion and thirst. However, fouling caused by the contact of blood with the artificial materials limits the time that devices with such materials can be usefully employed.

Fouling due to artificial surface-induced blood coagulation can be mitigated with anticoagulants but at unacceptable risk to the ambulatory patient. As a result, portable blood processing devices become impractical, and patients are generally forced to undergo the type of episodic dialysis schedule described above. A solution to these problems is needed if sustained, ambulatory treatment is to replace episodic dialysis.

The reasons for episodic treatment are many. For example, the bio-incompatibility, mentioned above, the lack of a portable device, the current need for blood circulation outside the patient, and the feeling of many patients that they are unable to manage the treatment process themselves (particularly because of the need to puncture the patient's blood vessels).

Thus, while daily dialysis (e.g., 1.5-2.0 hours, six days per week) or nocturnal dialysis (e.g., 8-10 hours, 6-7 nights per week) extends treatment times, many patients are unwilling or unable to use one of these forms of treatment.

Devices that provide for direct contact between blood and dialysis fluid for the purpose of treatment and analyte extraction have been proposed. For example, US Patent Pub. No. 2004/0009096 to Wellman describes devices in which blood and dialysate are in direct contact with each other. Another example, U.S. Pat. No. 5,948,684 to Weigl, relates to the application of analyte separation.

SUMMARY OF THE INVENTION

In general, the present invention features filters to introduce and remove extraction fluids from a microfluidic membraneless exchange device. Embodiments of the invention can be used for selectively removing undesirable materials from a sample fluid (e.g., blood fluid) by contact with a miscible fluid (e.g., extraction fluid or secondary fluid). In one embodiment, the pores of the filters are arranged in the device so as to substantially avoid contact with the blood fluid.

Sheathing a core of blood with the miscible fluid, or assuring that the miscible fluid lies between at least a substantial portion of the blood and the enclosing boundaries of the flow path, prevents, or at least limits, contact of the blood with these boundaries. Likewise, in some embodiments, the extraction fluid substantially inhibits contact between the blood and the filters. In turn, this configuration of the two fluids prevents, or at least reduces, the undesirable activation of factors in the blood, thereby reducing bio-incompatibilities that have been problematic in prior techniques of blood processing.

A microfluidic device, as considered in this application, has channels whose height is less than about 0.6 mm, where "height" is the dimension perpendicular to the direction of flow and also perpendicular to the interface across which transport occurs. As described in greater detail below, advantages are realized by using channels whose height is about 75 μm. However, channel heights can be a great as 0.6 mm. Smaller channel heights decrease the time needed to diffuse components from the sample fluid into the secondary fluid, resulting in higher performance and reduced device size as compared to larger channel heights. The secondary fluid, moreover, is generally miscible with blood and diffusive and convective transport of all components is expected. However, the diffusive and convective transport is accomplished without turbulent mixing of the sample fluid and the secondary fluid. The secondary fluid is withdrawn from the channels of the microfluidic device through thin barriers with pores, e.g., filters, having critical dimensions ranging from about one micrometer to about 50 nanometers.

As described above, the height of the extraction channel can be about 75 μm. Thus, the height of the two layers of extraction fluid and single layer of sample fluid (e.g. a blood fluid) are necessarily less than 75 μm. In one embodiment, the extraction channel is about 75 μm high and each fluid layer is about 25 μm high. The extraction fluids are introduced into the extraction channel in such a way as to maintain the extraction fluid along the walls of the extraction channel. The combination of extremely thin layers of fluid and the absence of a membrane along the diffusive interface result in high transport speeds as compared to those speeds obtained using membrane-based devices. Higher transport speeds allow for the total area of fluid contact to be relatively small as compared to membrane-based devices. Similarly, surfaces in contact with the blood fluid adjacent to the extraction channel, such as the blood fluid inlet channel surface before reaching the extraction region, can also be relatively small. Thus, the total amount of contact between the blood fluid and artificial surfaces is reduced. This aspect of the invention provides increased biocompatibility.

Withdrawing the miscible fluid (i.e., extraction fluid) from the microfluidic extraction channel through a filter prevents the build-up of certain components in the extraction fluid. For example, blood cells may migrate from the blood into the extraction fluid during the time when the fluids are in contact in the microfluidic extraction channel. In some operating scenarios, this migration is undesirable. As described in greater detail below, the characteristics of the fluid flows can be controlled to cause blood cells to concentrate in the middle of the blood fluid stream. This reduces the amount of blood cells that diffuse into the extraction fluid, but some cell migration may still occur. Appropriate pores in the filters inhibit departure of this small number of blood cells from the extraction channel with the extraction fluid. Moreover, the high shear rates characteristic of microfluidic flows provide a shear force at the surface of the filter sufficient to "sweep" this surface. Because the number of blood cells in the extraction fluid are kept relatively low, this sweeping action facilitates keeping the surface of the filter clear of blood cells, thus aiding in the preventing of clogging.

Similarly, other blood components can be inhibited from exiting the extraction channel with the extraction fluid. For example, the protein fibrinogen is capable of clotting, and it can be desirable in some embodiments to prevent fibrinogen from exiting the extraction channel with the extraction fluid. Thus, the pores of the filters can be sized to keep fibrinogen in the extraction channel, for example, by using filters with a pore size of about 50 nm. In addition, fluid flow characteristics, fluid interface velocity, and fluid contact time can be controlled to complement the selection of pore size in preventing loss of certain blood components and in preventing fouling.

Various embodiments also eliminate or at least substantially reduce the fouling reactions that have been known to be a major deterrent to the continuous use of an extracorporeal extraction device. In particular, as the primary transport surface in the membraneless exchange device (also referred to herein as a membraneless separator or extraction channel) is intrinsically non-fouling because of the increased biocompatibility and because the interface is constantly renewed. Thus, a major deterrent to long-term or continuous operation is removed, opening the possibility to the design and construction of small, wearable devices or systems with the recognized benefits of nearly continuous blood treatment. Such a device or system could be very small and worn or carried by the patient (e.g., outside of a hospital or clinic setting), and could be supplied with external buffer reservoirs (in a backpack, briefcase, or from a reservoir located in the home, located at the place of work, etc.). Further, because fouling would be reduced, and sustained operation at low blood flows over long times would be allowed, such anticoagulation as might be required could be administered as blood left the body and could be adjusted to have an effect confined to the extracorporeal circuit. As understood by those skilled in the art, avoiding systemic anticoagulation outside of the clinic is highly desirable.

Some of the devices, systems and methods described herein are capable of diffusing various blood components having different sizes. In addition, the flow of blood and a miscible fluid with which it is in contact can be controlled for the purpose of achieving the desired separation of cellular components. For example, as explained below, various flow conditions can be used that cause blood cells to move away from the blood-liquid interface, thereby making it possible to "skim" blood in order to remove substantial amounts of plasma, without cells. The filters aid in accomplishing this skimming effect by inhibiting the removal of cells that may have migrated into the miscible fluid despite the tendency of cells to move away from the blood-liquid interface at particular flow conditions.

As also discussed below, membraneless contact of a thin layer of blood with a extraction fluid can be used to cause high rates of exchange per unit area of blood-extraction fluid contact for all solutes. The discrimination among free (unbound) solutes will generally be less than the square-root of the ratio of their diffusion coefficients. While high exchange rates of particular substances are desired, indiscriminate transport is not. Therefore, a primary membraneless exchange device with filters on the extraction fluid outlets as described herein is used in conjunction with at least one secondary processor (e.g., a membrane device or other type of separator) in order to restrict the removal of desirable substances and effect the removal of undesirable substances from blood. The efficiency of such a secondary processor is greatly increased by the use of the primary separator that is capable of delivering cell-depleted (or cell-free) fractions of blood to it.

Therefore, in an example membraneless exchange device, transport of molecular components of blood to the extraction fluid can be indiscriminate. The extraction fluid, carrying both those molecular components that are, and are not, desirable to remove from blood, is provided to the secondary processor. The secondary processor regulates the operation of the membraneless separator through the composition of the recycle stream that it returns (directly or indirectly) to the extraction fluid inlets of the membraneless separator. Moreover, a membrane-based secondary processor used in this manner is able to achieve much higher separation velocities because cells, which are shear susceptible, are not present. Furthermore, concentration polarization (i.e., the accumulation of material rejected by the secondary processor on the upstream side of the separator) is limited to proteins and does not involve cells, and concentrations of proteins in the extraction fluid can be regulated by selection of filter pore size, fluid flow characteristics, and fluid contact time. Moreover, because cells would be retained in the primary separator (i.e., the membraneless exchange device), they would see artificial material only on its conduit surfaces, not on its liquid-liquid contact area, whence bio-incompatibilities should be much reduced. As such, it should be understood that the need for anticoagulation may be greatly reduced or eliminated.

Approaches to ameliorating the problems created by contact between the blood and an artificial membrane are described in U.S. patent application Ser. No. 10/801,366, entitled Systems and Methods of Blood-Based Therapies Having a Microfluidic Membraneless Exchange Device, filed Mar. 15, 2004, and U.S. patent application Ser. No. 11/127,905, having the same title, filed May 12, 2005, both herein incorporated by reference as if fully set forth in their entirety herein.

According to an embodiment, the invention is a method for exchanging components between a first fluid and a second fluid. The method begins with forming respective layers of first and second fluids such that diffusion-based exchange of components between the first and second fluids occurs in the absence of mixing. For example, the fluids can flow into a laminar flow channel. According to the method, at least a portion of the first fluid flows through pores sized to block first components from the second fluid while passing second components from the second fluid. For example, the first component could be blood cells, if the second fluid were blood and the second components could include large and small molecules such as albumin and electrolytes. In a more particular variation of this embodiment, the filtering includes passing the first fluid through pores whose size is smaller than 800 nm. In the case where the second fluid includes blood, the pore size is preferably smaller than this size and even more preferably, substantially less, for example, less than 600 nm.

Preferably the layers are formed by flowing the first and second fluids through a channel, and the filtering includes providing a filter forming a portion of a wall of the channel. Preferably the filter defines a smooth continuous surface that is coplanar with the wall of the channel. By doing this, the filter can remain clear of materials which may collect on the surface. This is particularly true where the channel has a small dimension in a direction normal to the surface of the filter, as is preferred, because the high shear rates of fluid resulting from the narrow space help to scour the surface of the filter. This feature is particularly preferred in embodiment where blood is the second fluid because proteins in the blood and cells might get stuck in a filter that does not have a relatively smooth surface. In addition, preferably, the pores define non-serpentine, non-branching channels.

In another preferred variation of the foregoing methods, there are two first layers with a second layer between them. In this way, the second layer may be sheathed by the first layer, if the channel within which they flow, has a suitable aspect ratio, which is preferred. Such a sandwich of flowing sheets of fluid provides high contact area and can provide a very low Reynolds number such that no mixing occurs, yet very effective diffusion between the layers is achieved. Preferably the channel's cross-section aspect ratio is greater than ten and more preferably, it is greater than 50. Preferably, the depth of the channel (the short dimension of the cross section) is between 75 and 500 microns and even more preferably, it is about 120 microns.

In a preferred variation of the foregoing method embodiments, the first fluid is generated by concentrating the second component in the filtered first component and recycling it back into the first layer or layers. This can be done by taking the filtrate from the filtering of the first fluid and passing it through fluid processor that removes fluid from the first fluid while leaving the second component behind. For example this can be done by ultrafiltration and recovering the filtrand and recycling the same. This can also be done, for example, by adding more of the second component to the recycled stream. For example, the second component could be serum albumin, where the second fluid it blood.

According to an embodiment, the invention is a method for clearing first components from a first fluid, comprising: flowing a layer of the first fluid surrounded by at least one co-flowing layer of solvent to isolate the layer from the wall of a conveying channel while permitting diffusion of the first component from the first fluid into the solute without mixing and removing the first component from the solvent and replenishing the co-flowing layer of solvent with a result of the removing. In an embodiment, the first fluid is blood. In the latter embodiment, the solvent is preferably an aqueous solution. The removing preferably includes filtering solvent by passing it through a filter and passing the resulting filtrate across another filter and recovering the filtrand therefrom, the fitrand being the result of the removing. The removing may include filtering solvent by passing it through a filter and passing the resulting filtrate across another filter and recovering the filtrand therefrom, the fitrand being the result of the removing. In an embodiment where the first fluid is blood, in a preferred embodiment, the removing includes filtering the solvent to block blood cells. For example, where the first fluid is blood, the removing may include dialyzing the solvent at a location remote from blood cells and returning the dialyzed solvent to the co-flowing layer to permit the diffusion of blood proteins back into the blood.

According to an embodiment, the invention is a method of processing blood. The method includes concurrently flowing blood and an aqueous solvent through a channel with a wall portion having a regular pattern of pores in a wall thereof, the pores having a maximum size less than 1 micron. The method further includes circulating the solvent through a flow circuit that includes the pores and returns the solvent back to the channel at a point upstream of the pores. The flow circuit preferably includes a processor that removes water from the solvent and more preferably, also removes uremic toxins from the solvent. Preferably, the pores have a maximum size of less than 600 nm.

Preferably, in the latter embodiment, the flowing creates a flow that keeps blood cells from contacting substantially all of the wall surface. Preferably, the pores have a maximum size of about 100 nm or less. The concurrently flowing preferably includes flowing blood and aqueous solvent at approximately equal volume rates in the channel.

According to another embodiment the invention is a fluid processing device with a channel having a ratio of width to depth of more than 10. The depth is no more than 300 microns and both the width and the depth are perpendicular to a direction of flow. The channel has an input end and an output end separated by a length, which is parallel to the direction of flow. Two inlet extraction fluid ports and one inlet sample fluid port, located between the two inlet extraction fluid ports, are positioned proximal to the input end and two outlet extraction fluid ports and one outlet sample fluid port between the two outlet extraction fluid ports are positioned proximal to the output end. The outlet extraction fluid ports having first filters. At least one of the outlet extraction fluid ports is coupled by a flow channel, other than the channel, to at least one of the inlet extraction fluid ports.

Preferably, the channel has a wall surface with dimensions are equal to the width and the length, the first filters forming a portion of the wall. Preferably, the first filters have a pore size no greater than 1000 nm, more preferably, no greater than 800 nm and even more preferably, no greater than 300 nm. Preferably, the channel has a depth of no more than 120 microns. In a preferred variation, the aforementioned ratio of width to depth is more than 50. In a variation, the embodiment has at least one pump configured to pump at least 1 liter of blood and at least one liter of solvent through the channel during a treatment cycle lasting no more than one day.

In a particularly preferred variation of the foregoing embodiments, the inlet and outlet sample ports are connected to channels with connectors connectable to arterial and venous lines of a patient access.

According to another embodiment, the invention is a device for exchanging components between a first fluid and a second fluid, where the second fluid contains first and second components. The device includes a channel that receives a first fluid and a second fluid to form at least one first layer and at least one second layer of the first and second fluids, respectively, such that they are in direct contact with each other and do not mix. The at least one first layer and at least one second layer flow in a same flow direction. The channel has outlets with at least one filter that receive only the first fluid, the at least one filter having pores sized to block the first components from the second fluid while passing the second components from the second fluid. Preferably, the at least one filter has pores whose size is smaller than 800 nm. The channel has walls and the at least one filter preferably defines a portion of the channel wall. In a preferred variation, the at least one first layer is two layers and the at least one second layer is one layer, the second layer being positioned between the two first layers. Preferably the pores define direct channels which are non-serpentine and non-branching. In a preferred embodiment, the first components are erythrocytes.

The first fluid preferably includes a fluid obtained by increasing the concentration of the second component in a filtrate obtained from passing the first fluid through the at least one filter. Preferably, the second component includes serum albumin. Preferably, the channel has walls and the at least one first layer is two first layers and the forming includes forming the two first layers with a single second layer between them such that the first fluid prevents the second fluid from directly contacting the walls. Preferably, the channel may have a cross-section cutting across the flow direction whose aspect ratio is greater than ten. Preferably, the channel has a depth across the flow direction between 75 and 300 microns. Most preferably, the depth is about 120 microns.

According to another embodiment, the invention is a device for exchanging components between a first fluid and a second fluid. The device has first and second channels, each having respective inlets and outlets to permit at least two fluids flowing into the inlets to flow co-currently therethrough, in direct contact with each other, and to flow out of the outlets. The device further contains a fluid processor, with an inlet and an outlet, which changes a property of fluids received at the inlet and conveys a changed fluid to the outlet. A first of the first channel outlets is connected to a first of the second channel inlets. A second of the first channel outlets is connected to the fluid processor inlet. A second of the second channel inlets is connected to the fluid processor outlet.

Preferably, the fluid processor includes a membrane, for example, a dialyzer. A fluid conveyance may be provided to cause fluids to flow through the first and second channels in laminar fashion such that transport between the fluids in the channels is primarily by diffusion. Preferably, the second of the first channel outlets contains a filter. Preferably the filter has pores whose sizes are a maximum of 600 nm.

According to an embodiment, the invention is a method of separating blood cells from plasma. The method includes drawing most of the blood cells, in a layer including blood cells and plasma, away from a vessel surface having a filtered outlet and removing the plasma through the filtered outlet to block blood cells entering the outlet. In an embodiment, the layer is a flowing layer and in a variation of the embodiment, the drawing includes creating a shear gradient in the flowing layer that is higher near the wall than remote from the surface. Preferably, the layer includes an aqueous solvent. The filtered outlet preferably has a filter with a surface that is coplanar with the vessel surface. In this case, where the layer is a flowing layer having a shear near the surface, the shear scours the surface of the filter.

Further features of the invention, its nature and various advantages, will be more apparent upon consideration of the following detailed description, taken in conjunction with the accompanying drawings, in which like reference characters refer to like parts throughout.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention.

DETAILED DESCRIPTION OF THE INVENTION

An exchange device extracts selected components from a sample fluid. The exchange device passes an extraction fluid and a sample fluid in laminar flow through a common extraction channel such that the extraction and sample fluids come in direct contact, but remain in defined layers throughout the common extraction channel. Preferably, the extraction channel has dimensions that assure laminar flow conditions are maintained even under conditions of normal use and that permit a large interface area between the sample and extraction fluids in a compact design. As such, the channel and its related components have the dimensions which may be characterized by the term, microfluidic.

Figure 1A:
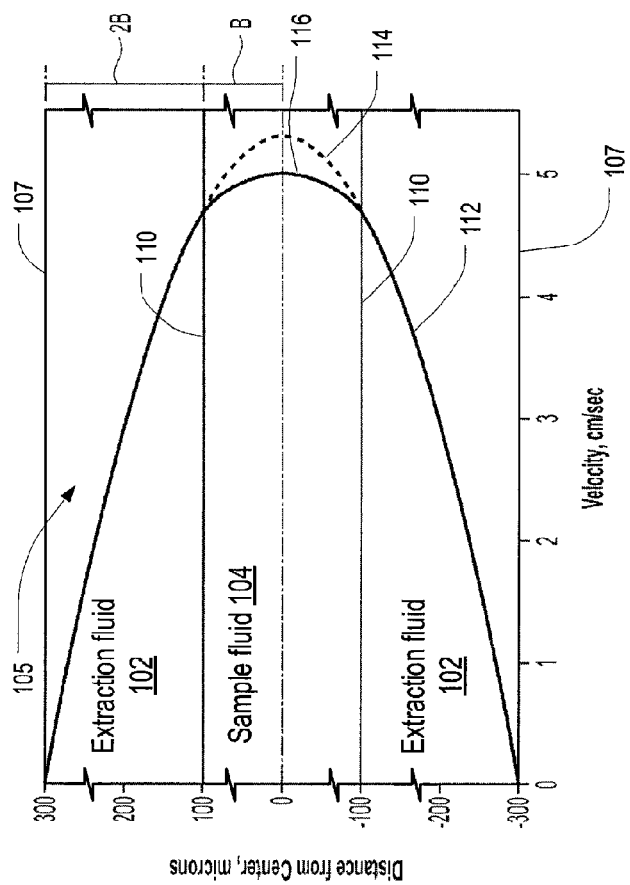
FIG. 1A shows the velocity profile of a core stream of blood sheathed on both of its sides by an extraction fluid calculated for blood with a viscosity assumed twice that of the extraction fluid and with a centerline velocity of 5 cm/sec.
Figure 1B:
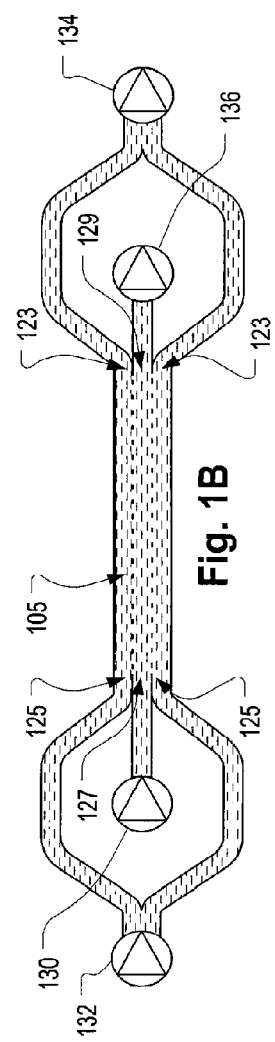
FIG. 1B is a figurative illustration of an extraction channel.

Referring to FIGS. 1A and 1B, in a preferred configuration, the sample fluid 104 is blood, which flows in a layer that is sandwiched between two extraction fluid layers 102 all of which flow together through an extraction channel 105. Relative to the oriented drawing page in FIG. 1A, the extraction channel 105 has a width going into the page, a length in the horizontal direction, and a depth in the vertical direction. Generally, as used herein, the term "width" refers to a dimension perpendicular to the direction of flow and parallel to the interface between the two liquids, "depth" refers to a dimension perpendicular to the direction of flow and to the interface between the two fluids, and "length" refers to the dimension parallel to the flow direction. Superimposed on the extraction channel 105 is a graph, with axes, to show the velocity profile of the sample 104 and extraction 102 fluid layers.

The flow in the extraction channel 105 creates two liquid-liquid boundaries 110 between the sample fluid 104 and the two extraction fluid 102 layers. The extraction channel 105 can be configured so that it substantially isolates the sample fluid 104 from the artificial walls 107 of the extraction channel 105 while the sample fluid is in the extraction channel 105.

For example, in a preferred configuration, the extraction channel 105 is many times wider and longer than it is deep. As a result, the sample fluid 104 contacts the extraction fluid 102 over a large area (length×width), but contacts the artificial walls 107 of the channel over a much smaller area (length×depth=2B of sample layer) at the lateral edges. This helps to provide a large interface between the sample 104 and extraction 102 fluids and effectively isolates the sample fluid 104 from the walls of the extraction channel.

A preferred extraction channel 105 has inlets 125 which convey fluid into the extraction channel 105 adjacent the walls 107. The extraction channel includes respective outlets 123, displaced in a length direction from the inlets 125, which draw extraction fluid 102 from the extraction channel 105. The sample fluid 104 flows into and out of an aligned inlet 127 and outlet 129, respectively. The details of embodiments of the inlets and outlets 123, 125, 127, and 129 are described with respect to embodiments below. In a preferred embodiment of an extraction channel 105, usable for renal replacement therapy, the sample fluid 104 is blood and the extraction fluid 102 is an aqueous solution such as dialysate. As explained in more detail below, the blood cells tend to remain in the sample fluid 104 layer because they diffuse more slowly than small particles, such as proteins and ionic species. Cells are also subject to tendency to migrate toward the low shear regions of the flow, which is at the center of the extraction channel 105. (The tendency of cells to migrate to low shear regions is described in Goldsmith, H. L. and Spain, S., Margination of leukocytes in blood flow through small tubes, Microvasc. Res. 1984 March; 27(2):204-22.) In a preferred embodiment, cells, or other large particles, may also be blocked from exiting the extraction fluid outlets 123 by filters (not shown in FIGS. 1A and 1B), which are described in more detail below.

The velocity profile 112/114 is calculated for a situation where the properties of the sample fluid 104 are the same as for the extraction fluid 102. The velocity profile 112/114 is consistent with the classic single fluid profile assumed by a laminar flow in a two-dimensional channel. The velocity profile 112/116, however, exhibits blunting, which results when the sample fluid 104 has a higher viscosity than the extraction fluid 102. This is the case when the sample fluid 104 is blood and the extraction fluid 102 is dialysate. Note that FIG. 1A shows a calculated condition for the situation where there is a substantially clear boundary 110 between the sample 104 and extraction 102 fluids. In an actual device, the properties of the fluids may blend as the boundaries 110 become less distinct due to diffusion of fluid components thereacross.

Transport of molecules within the extraction channel 105 is preferably non-turbulent with no mixing. By providing a flow configuration with selected flow rates and a channel size, mixing can be reliably prevented. If configured to function as a dialyzer, the device enables treatments with brief contact time between blood and artificial materials, low extracorporeal blood volume, and very compact size in a microfluidic device. Note that as used herein, the term "extracorporeal" is not necessarily limited to the removal of blood from the patient body envelope and microfluidic extraction channels that are implanted in the bodies of patients are not intended to be excluded from the scope of the invention.

In a renal replacement therapy embodiment, where the sample fluid 104 may be whole blood, it is contemplated that only non-cellular components of the blood are extracted by the extraction channel 105. The flow of extraction fluid 102 in the extraction channel 105 can be controlled independently of the flow of blood in the extraction channel 105 using an appropriate combination one or more injection pumps 130 and 132, and withdrawal pumps 134, 136. For example a first injection pump 132 may inject extraction fluid 102 into the extraction channel 105 and a first withdrawal pump 134 may withdraw extraction fluid 102 out of the extraction channel 105. Similarly respective injection and withdrawal pumps 130 and 136 may inject and withdraw sample fluid 104 into and from the extraction channel 105, respectively. By controlling the relative rates of the pumps 130-136, the change in total volume of the blood exiting the extraction channel 105 can be varied. In a blood treatment embodiment, the control of the inflow and outflow rates is used to regulate a patient's fluid volume, which is a conventional requirement of renal replacement therapy. In this embodiment, the extraction channel depth (6B as shown in FIG. 1) is preferably in the range of 70 to 300 µm and more preferably, approximately 120 µm. Preferably, the extraction channel 105 has a width-to-depth ratio of at least ten. Preferably, width-to-depth ratio is greater than 50 and more preferably greater than 500. Note that although the figurative depiction in FIG. 1B shows four pumps, other embodiments could employ a smaller or greater number of pumps.

Referring to FIG. 1A, the velocity profile 112/114 of the core sample fluid 104 layer, sheathed on both of its sides by the extraction fluid 102 layers, is calculated for blood with a viscosity, $\mu_B$, assumed to be twice that of the extraction fluid, $\mu_S$ and with a centerline velocity of 5 cm/sec. At this centerline velocity, a flow path length of 10 cm would result in a contact time of slightly longer than 2 sec. The diffusion of constituent particles (of all sized, from small ions to cells) resulting from steady contact of two moving liquids for an exposure time determined by the length of their contact area divided by their interfacial velocity ($\tau=L/v$) is analogous to the instant exposure of one volume of stagnant fluid to another for a specified time. Thus, what happens to the flowing fluids along their shared flow path is comparable to what happens to two stagnant fluids exposed to each other for a finite period of time. The stagnant fluid problem was solved by Loschmidt in 1870.

$$E = \frac{1}{2} - \frac{4}{\pi^2} \sum_0^\infty \frac{1}{(2n+1)^2} \exp\left[-(2n+1)^2 \left(\frac{\pi}{2B}\right)^2 Dt\right]$$

for which the zeroth order term, $$E = \frac{1}{2} - \frac{4}{\pi^2} \exp\left[-\left(\frac{\pi}{2B}\right)^2 Dt\right]$$

suffices when $$\left(\frac{\pi}{2B}\right)^2 Dt > 0.7$$

This formula greatly simplifies the estimation of how much mass can be transferred between fluids in a membraneless system. In particular, this formula provides an approximation of the extraction E of a component with a diffusion coefficient D when two liquids flow side-by-side and remain in contact for an interval of time, t.

Figure 2:
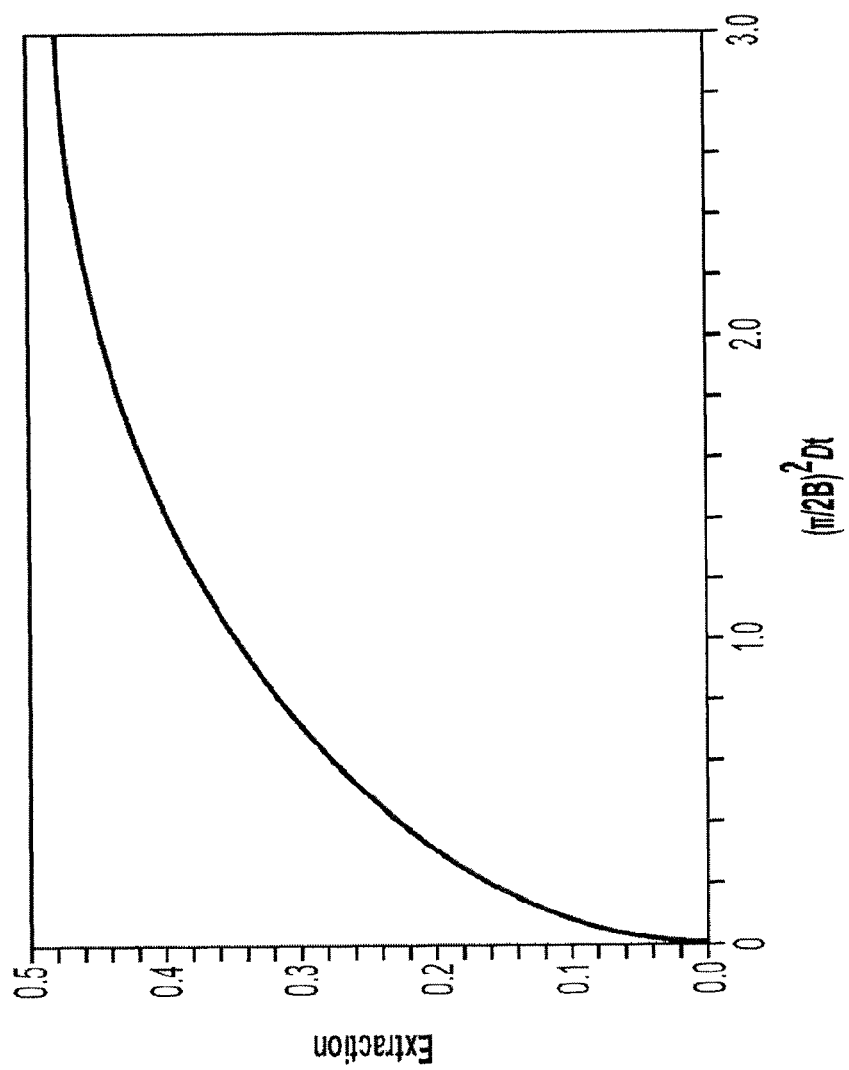
FIG. 2 shows a plot using Loschmidt's formula of 1870, describing diffusive exchange between two fluid layers, each fluid layer has the same thickness, B.

FIG. 2 shows a plot of extraction versus $$\left(\frac{\pi}{2B}\right)^2 Dt$$

using a version of Loschmidt's formula, where each fluid layer has the same thickness B (i.e., B is the half-thickness of the sheathed layer of sample fluid). The situation shown in the plot of FIG. 2 can be interpreted as a blood layer, of thickness B, contacting a layer of extraction fluid (i.e., extraction fluid). The sheathing layer is presumed to be at zero concentration and E is the fraction of material in the blood layer that is extracted in a time t, where D is the diffusion coefficient of the extracted substance. If a layer of thickness twice B is bounded on both sides by fluid layers of thickness B, the formula still applies, as written. As indicated by this formula, E cannot exceed 0.5 since, in co-current flow, the highest extraction corresponds to equilibrium of the two fluids.

If 90% of the maximum possible extraction (which is E=0.45) is desired, the ratio Dt/B must be approximately 0.86. Any combination of diffusion coefficient, blood layer thickness, and exposure time that produces this value, will produce the same extraction. Moreover, it can be shown that the necessary area (2LW) to achieve this extraction equals 0.86 BQ/D, where Q is the blood (and extraction fluid) flow rate. Thus, for urea (D=10 cm at a blood flow rate of 0.300 cm³/s) the required area is 2.58·B·10⁴ cm². If B is taken to be 100 µm, the required area is 258 cm². This flow corresponds to what might be needed in a wearable artificial kidney. If, instead, a conventional flow rate of 5 cm³/s were used, the required area would be 4300 cm². If thinner films are used, even less area is required to reach a specified extraction.

In terms of extraction, combinations of length L and width W may be varied to produce the required area and a specified extraction rate. (If one assumes D for albumin to be 5·10⁻⁷ cm²/s, its extraction would be 0.116, 26% of that for urea.) An increase in channel depth raises the requisite contact time and may tend to reduce the stability of the sheathed flow. When total blood layer thickness is 25, 50, or 100 µm, and the blood flow is 20 ml/min (as it might be with a wearable artificial kidney), the interfacial area needed to cause a substance, such as urea (5·10⁻⁷ cm²/s) to reach 90% of equilibrium is, respectively, 18, 36, and 71 cm². Thus, as these examples show, in certain embodiments, it is desirable to have a total blood layer thickness of about 25 µm. Although desirable, this thickness is not essential and other considerations may make it desirable to provide for a different blood layer thickness in a blood treatment embodiment. Also, the above calculations apply to a dialysis-type blood treatment. As noted, however, the invention can be applied to other types of exchange processes and fluids.

It should be noted that use of the Loschmidt formula with flowing systems introduces an incongruity that prevents precise estimation of mass transfer rates and clearances, given that it presumes that both fluids are moving at uniform velocity. In particular, it provides an excellent approximation for the sheathed fluid (blood), but ignores the nearly linear decay in velocity with distance from the interface in the extraction fluid. Nevertheless, the Loschmidt formula is adequate for design purposes when the sheathing layer has a total thickness (2B) that is twice that of its half of the blood layer (B) (as shown in FIG. 1A), and thus a rate of flow nearly equal to its half of the central stream.

A shear-induced self-diffusion coefficient of cells $D_{particle}$ can be estimated by using an expression provided by Leighton and Acrivos (1987) for concentrated suspensions: $D_{particle} \propto \phi^2 a^2 \gamma^2$, where $\phi$ is the particle volume fraction, a is the particle radius, and $\dot{\gamma}$ is the shear rate. Then, the characteristic displacement of a cell can be expressed as $\Delta y \propto \sqrt{D_{particle} t}$. Choosing representative values for the layered flow system such that the cell volume fraction $\phi \cong 0.45/2 = 0.225$, the average radius a of the red blood cell$\cong 2.5$ μm, and the average shear rate $\dot{\gamma}$ over the blood layer$\cong 3$ to 28 s$^{-1}$ (based on an average velocity range of 0.5 to 5 cm/s), we calculate that $D_{particle} \sim 10^{-8}$ cm$^2$/s, which is approximately three orders of magnitude smaller than the typical diffusion coefficient of small solutes. Based on this value of the shear-induced diffusion coefficient (and assuming 10 sec of contact between layers), it is estimated that blood cells are displaced by a characteristic distance $\Delta y \cong 3$ to 9 μm from the central layer, depending on the choice of blood velocity and the concomitant shear rate. This low distance of cell migration away from the central layer facilitates the removal of cell-free portions of the blood.

For a number of reasons, a membraneless extraction channel 105 that relies solely upon the differences in the diffusion rates of small versus large particles (that is, small molecules versus macromolecules or even cells) may not be sufficiently discriminating to provide a basis for blood treatment. For example, a practical system for renal replacement therapy preferably prevents the sample fluid 104 retrieved from outlet 129 from being depleted of a significant fraction of the macromolecules, such as serum albumen, entering at inlet 127. In addition, the system should also prevent the loss of blood cells. In the embodiments discussed below, additional features are combined with the extraction channel discussed above, to provide benefits of a direct contact exchange but with the high degree of discrimination normally associated with membranes.

Figure 3:
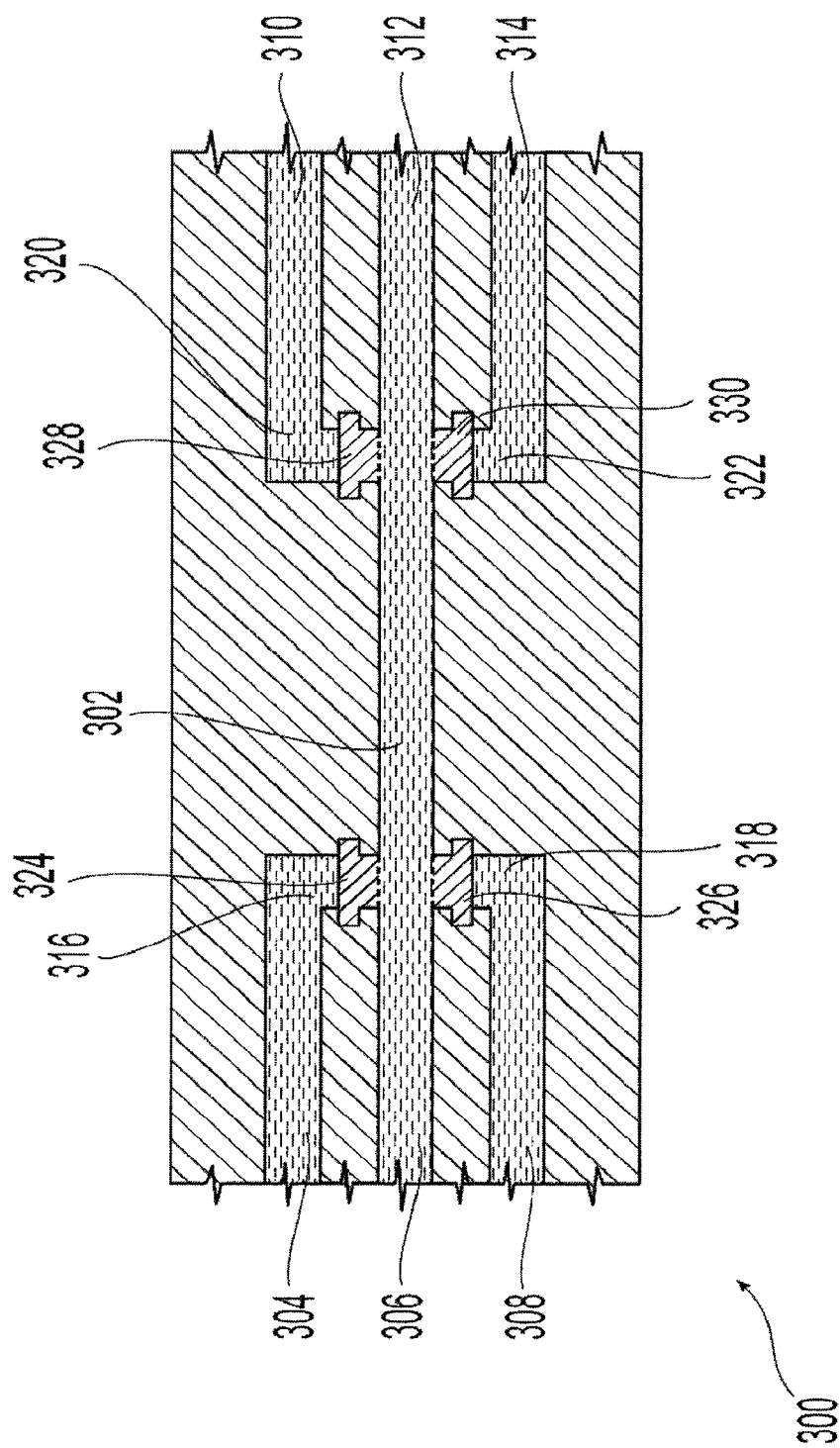
FIG. 3 shows a simplified view of a membraneless separator with filters in the extraction fluid inlets and outlets.

FIG. 3 shows a simplified side view of an extraction channel 300. The extraction channel can be created using various techniques, for example, using wEDM (wirecut electric discharge machining) methods. The illustrated embodiment includes an extraction channel 302 which receive fluids from three separate inlet channels 304, 306 and 308. Fluid from the extraction channel 302 leaves the channel through three respective outlet channels 310, 312 and 314. Inlet channel 304 has an opening 316 connecting inlet channel 304 to extraction channel 302. Likewise, inlet channel 308 has an opening 318 connecting inlet channel 308 to extraction channel 302. Outlet channels 310 and 314 have corresponding openings 320 and 322 to extraction channel 302. Extraction fluid flows along the top surface of the extraction channel in a laminar fashion from inlet channel 304 to outlet channel 310 and in a similar fashion along the bottom surface from inlet channel 308 to the outlet channel 314.

Figure 4:
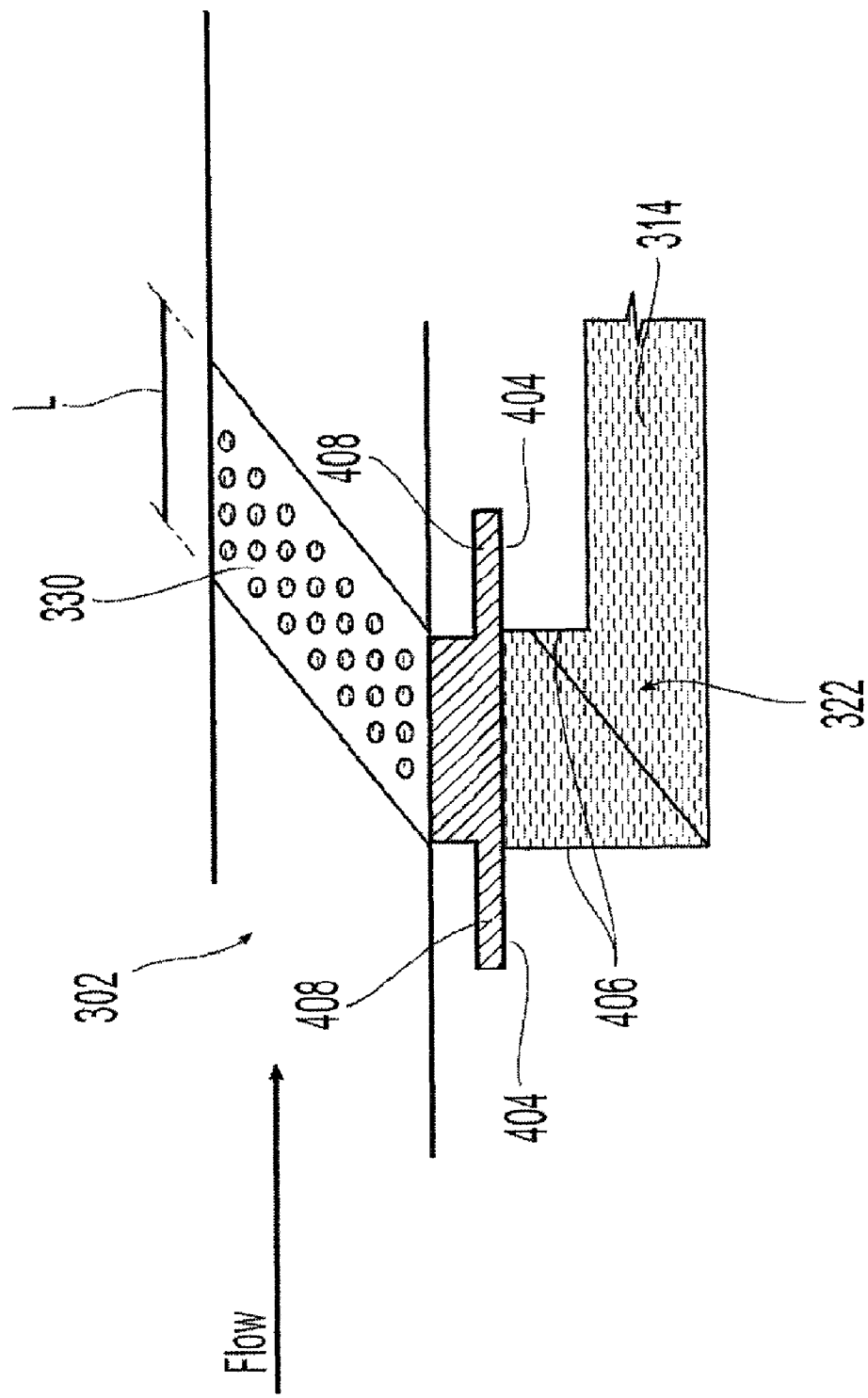
FIG. 4 shows a partial close-up perspective view of an area around an opening of an outlet channel, including a filter, of the membraneless separator of FIG. 3.

Filters are preferably placed in all or some of openings 316, 318, 320, and 322 by which extraction fluid enters and leaves the extraction channel 302. For example, in the embodiment of FIG. 3, filters 324 and 326 are located in openings 316 and 318 of inlet channels 304 and 308, respectively and filters 328 and 330 are located in openings 320 and 322 of outlet channels 310 and 314, respectively. The length of extraction channel 302, between filter 326 and filter 330, is preferably about 1-2 cm. The length of the filters can be about 3-4 mm (as shown by L in FIG. 4). An aggregate extraction channel width, for example 30 cm, can be obtained by running multiple extraction channels in parallel. FIG. 4 shows a partial close up perspective view of the area around opening 322 of outlet channel 314 of extraction channel 300 of FIG. 3. A filter 330 is placed in opening 322 connecting outlet channel 314 with extraction channel 302. In one example embodiment, filter 330 has a cross-section in the shape of an inverted "T", as shown in the figure. Opening 322 of outlet channel 314 has two opposed grooves 404 formed in side walls 406 of opening 322. Grooves 404 receive two opposed tabs 408 of filter 330. This design enables filter 330 to be installed by sliding the filter 330 into place. Likewise, the filter 330 can be removed from outlet channel opening 322 by sliding the filter 330 out of the outlet channel opening 322. Thus, this example design allows for easy replacement of filter 330.

Filter 330 can be of such size and shape as to eliminate gaps between opening 322 and filter 330, thereby forcing the extraction fluid to flow through the pores in the surface. Alternatively, the filters can be fitted in recesses with upstream and downstream steps to support them such that a flat surface is of the filter faces the extraction channel 302. Various techniques can be used to gain access to opening area 322 in order to install or remove filter 330. For example, the side of extraction channel 300 can be sealed with a removable plate. Thus, by removing the plate, one can gain access to openings 316, 318, 320, and 322. Various mechanical mounting configurations for the filters are possible including the integral formation of the filters in the materials used to create the channels 304, 306, 308, 302, 310, 312, and 314.

Note that in a blood treatment device, filters 328 and 330 are preferably provided to ensure against the migration of blood cells into the extraction fluid outlet channels 310 and 314. Inlet filters 324 and 326 may also be provided to guard against introduction of larger particles into the extraction channel 302 and to smooth the flow of extraction fluid into the extraction channel 302. The size of the pores shown in filter 330 are greatly exaggerated for the purposes of illustration only. Preferably, the actual pore size is less than 1000 nm in diameter and more preferably, 600 nm or less. Even more preferably, the size is about 100 nm, but may be still smaller, for example, 10 nm.

Figure 5:
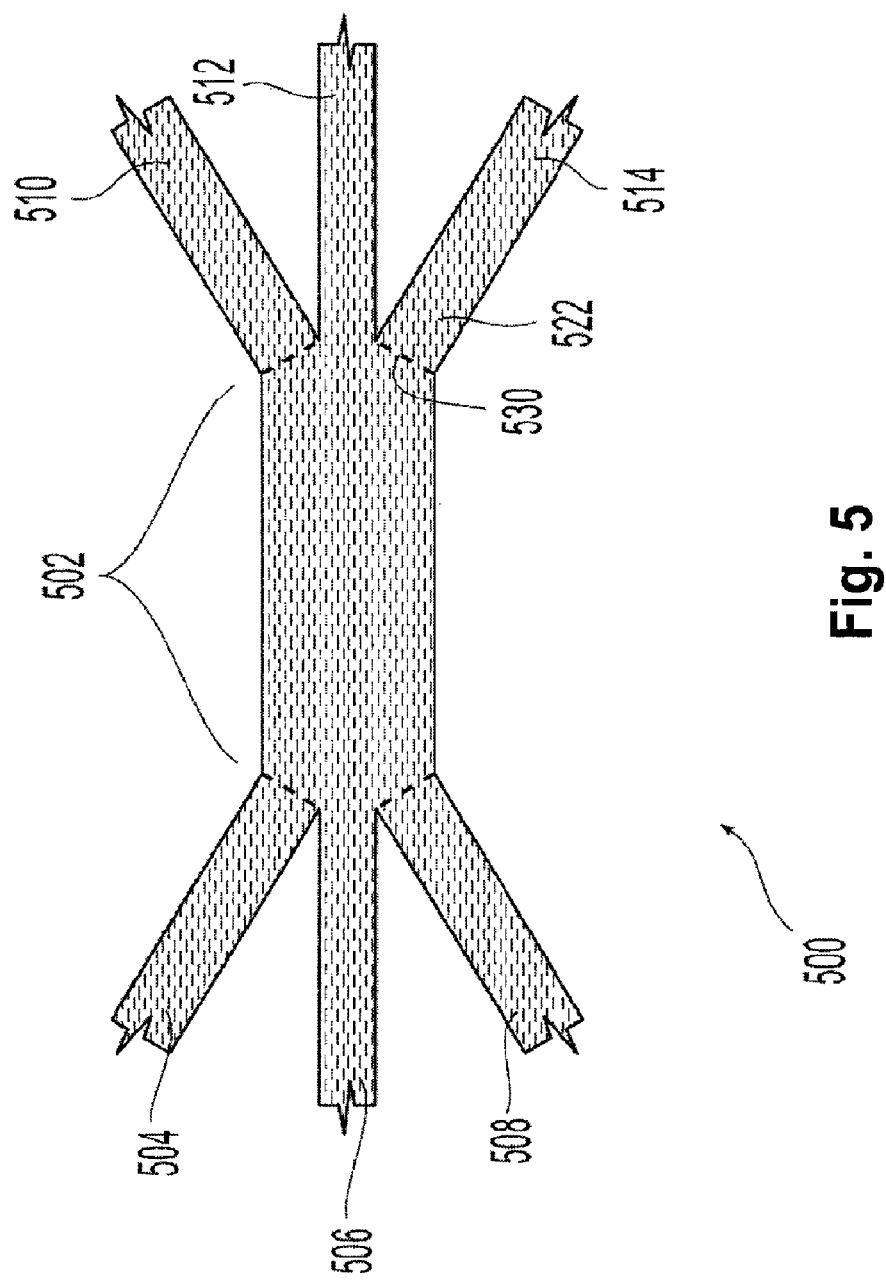
FIG. 5 shows an outline of another possible embodiment of a membraneless separator.

The particular fabrication process described above is for purposes of illustration only. For example, the dimensions of extraction channel 300 may be altered without departing from the scope of the present invention. FIG. 5 shows an outline of another embodiment of an extraction channel 500. sample fluid enters an extraction channel 502 through inlet channel 506 and leaves through outlet channel 512. In this example, inlet channels 504 and 508 and outlet channels 510 and 514 do not form 90-degree angles with the length of the extraction channel 502. Thus, for example, the opening 522 and the filter 530 of outlet channel 514 faces the direction of flow.

Figure 6:
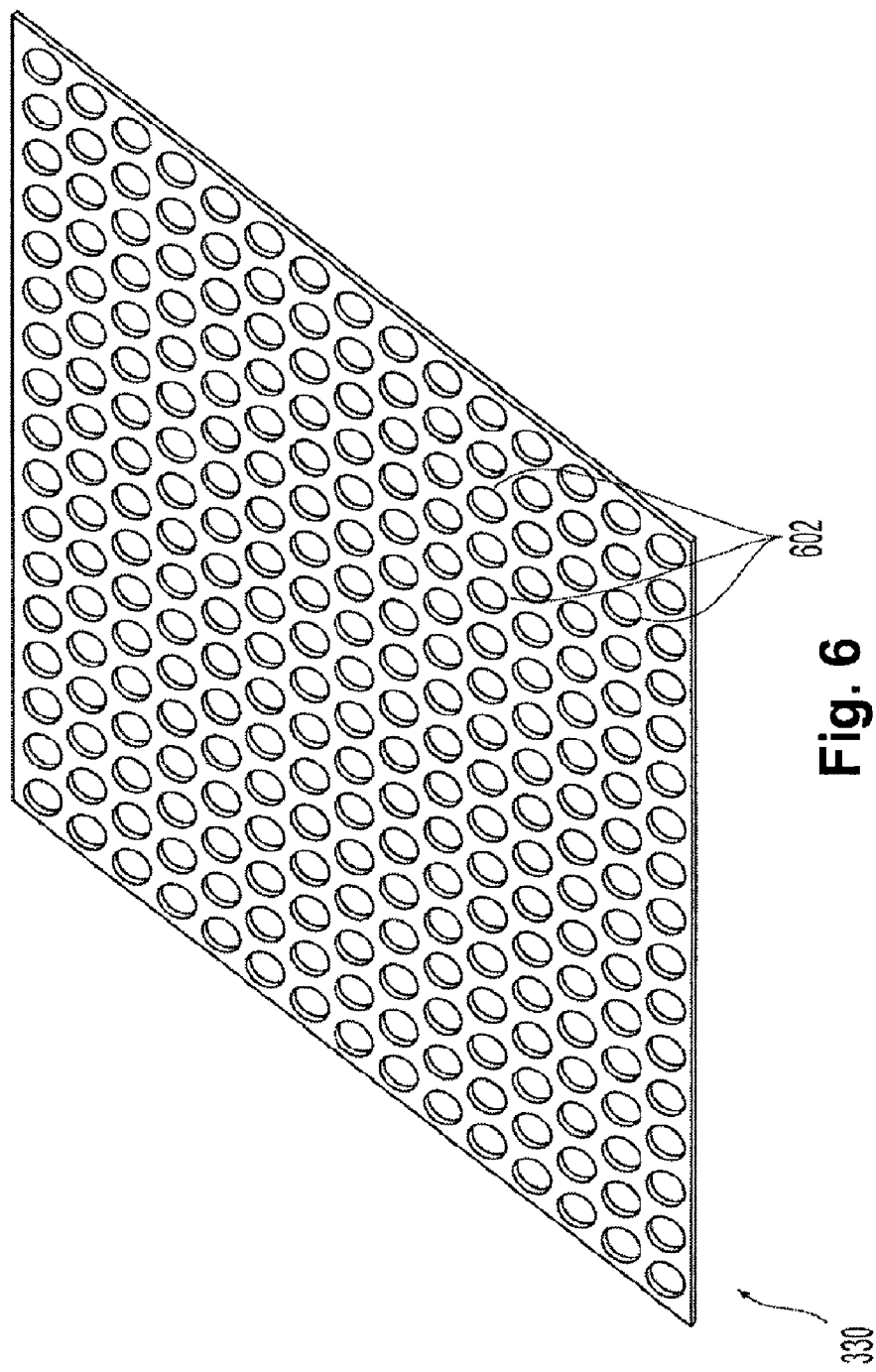
FIG. 6 shows an example of a filter.

FIG. 6 shows an example of filter 330. Filter 330 contains pores 602 selectively sized to exclude components having a particle size larger than the pore diameter. The diameter of pores 602 can vary according to the components intended to be excluded from outlet channel 310 and 314. The diameter of pores 602 can range from several micrometers to about 10 nm. Thus, although a variety of components of the sample fluid can migrate into the extraction fluid layers while the fluids are in the extraction channel, the filters prevent certain particles from leaving the extraction channel via the outlet channels. For example, if embodiments of the invention are to be used in a dialysis process to remove substances from human blood, a filter pore size of, for example, about 300 nm can be selected to exclude blood cells, thereby preventing the loss of blood cells from the blood fluid being treated, while simultaneously avoiding contact between the blood fluid and the filter.

As mentioned above, filters can be included in openings 316 and 318 of inlet channels 304 and 308. Including filters in these openings helps to stabilize the introduction of extraction fluid by facilitating an even distribution of fluid into extraction channel 302. As with filters 328 and 300 in outlet channels 310 and 314, a shear flow across the surface of the filter is preferably maintained. In addition, the filters prevent ingress of undesirable components into inlet channels 304 and 308. The filters may be particularly useful in embodiments in which there are periods of time when there is no extraction fluid flow, but a sample fluid is flowing into extraction channel 302 via sample inlet 306. Although the pore size of a filter at the outlet and inlet may be uniform across a given filter, the pore size of an inlet filter may be different from that of an outlet filter.

One example of a commercially available device which can be used for the filters described above is a microsieve micro filtration device (available from Aquamarijn Micro Filtration BV, Berkelkade 11, NL 7201 JE Zutphen). These filters surfaces can be created using photolithographic silicon chip manufacturing techniques and other techniques. For example, a filter can be created by coating a 600 μm thick silicon wafer with a layer of silicon nitride approximately 1 μm thick. A pore pattern can then be created in the silicon nitride layer using current state-of-the art photolithographic masking and etching techniques. After etching the silicon nitride layer, the silicon layer can then be roughly etched to expose the underside of the silicon nitride layer, thereby creating a flow path through the pores. Some silicon is allowed to remain during the etching process in order to provide support for the relatively thin silicon nitride layer. Also, the filter component may include multiple parts, such as the filter 330 along with a support component (not shown) to which it can be adhered.

The properties desired in the filters include a smooth and regular surface to permit the extraction channel flow to scour them clean and to help prevent the trapping of cells or macromolecules on the surface facing the extraction channel. In addition, the channels defined in the filter preferably form a regular array which are preferably non-serpentine, preferably non-branching. Preferably, also, the filters define a smooth and direct flow path for the filtered fluid and a smooth surface facing the flow inside the extraction channel. The filter, including any support structure, should also be such that particles flow directly through the pore channels without adhering or being trapped in small surface features. The technology for creating such filters and the materials of which they are made, are numerous and it is expected that they will continue to be developed and refined. The invention is not limited to any particular method for making or structure for the filters, though the properties described are preferred for embodiments in which blood or blood fluid is processed.

Figure 7:
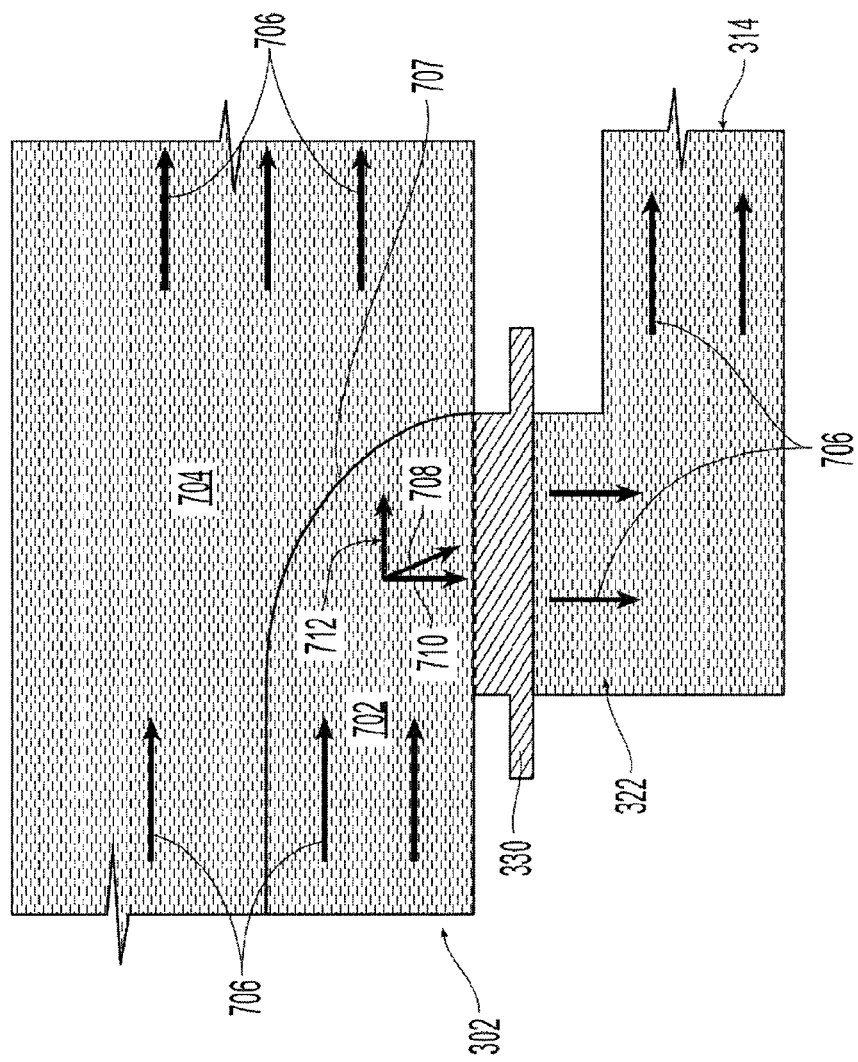
FIG. 7 shows a close-up side view of a filter illustrating a fluid sweeping action across the surface of the filter.

FIG. 7 shows a close-up side view of the area around opening 322 of outlet channel 314 shown in FIG. 3. In the figure, an extraction fluid layer 702 is shown flowing along the bottom of extraction channel 302, and a sample layer 704 is shown flowing on top of extraction fluid 702. Flow lines 706 indicate the direction of flow. As extraction fluid 702 is drawn through filter 330, the extraction fluid layer is drawn down toward the filter 330 as indicated by the curved boundary 707 of the extraction fluid layer 702. The extraction fluid 702, as it approaches the filter 330, has a downward flow component 710 and a forward flow component 712, the resultant being shown at 708. Forward flow component 712 acts to sweep the surface of filter 330. Thus, any components contained in extraction fluid 702 that gather along the surface of filter 330 are swept along the surface of filter 330 in the direction of forward flow component 712. This sweeping action eventually returns the excluded components to sample layer 704.

Note that the border 707 is not precisely representative of the flow pattern and is intended merely suggest that the extraction layer 702, which sheaths the sample layer 704, is substantially drawn into outlet channel 314. Also note that the boundary between extraction 702 and sample 704 layers is not well-defined. In fact, in an embodiment, the extraction channel 302 is constructed such that all the components are substantially blended except for blood cells, which tend to migrate toward the central low fluid shear region of the extraction channel flow 702.

Figure 8:
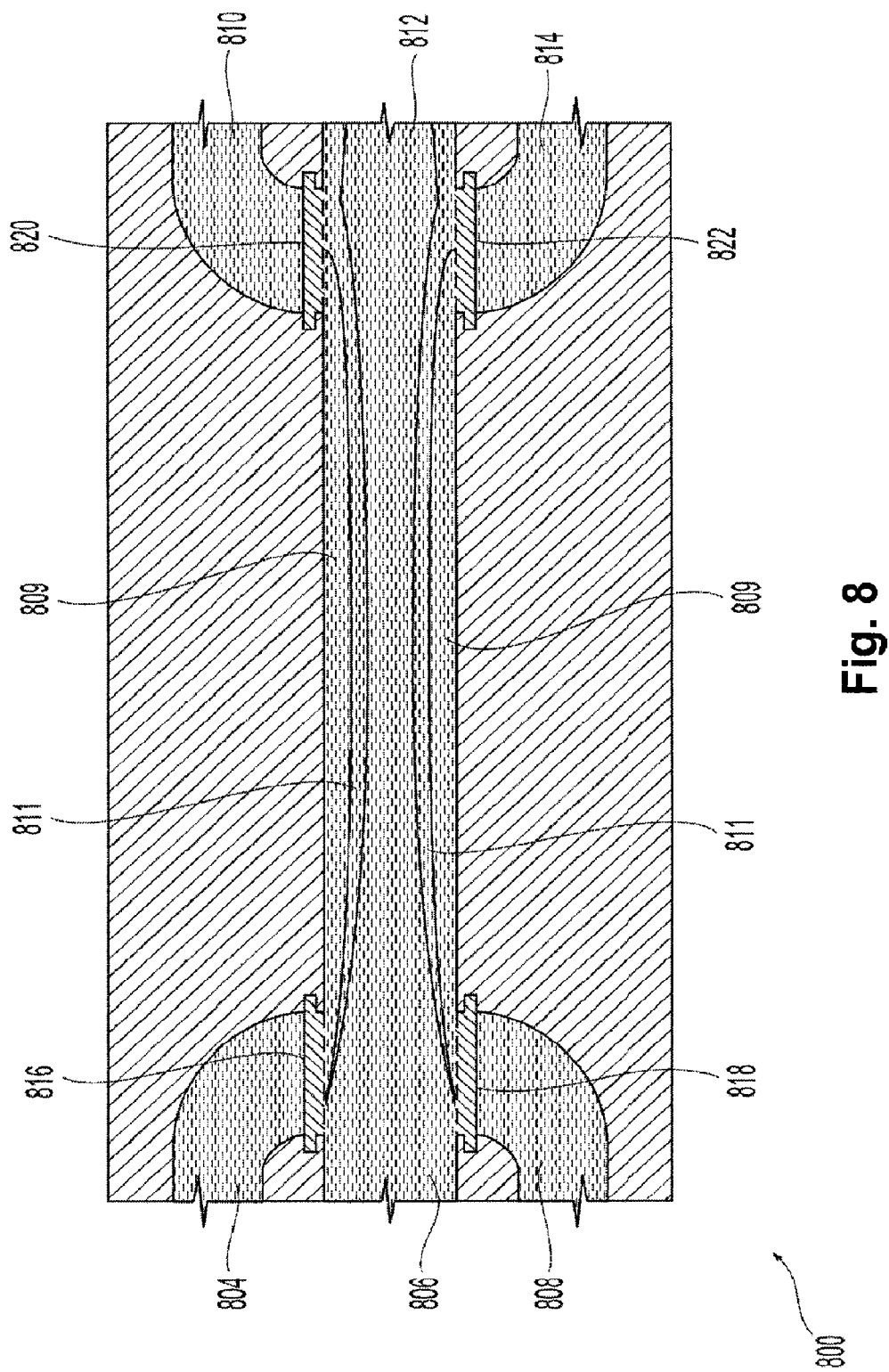
FIG. 8 shows a membraneless separator with filters used for the purpose of plasmapheresis.

FIG. 8 shows a membraneless separator 800 that is similar to the device 300 described above. The membraneless separator 800 includes an extraction channel 802, three separate inlet channels 804, 806 and 808 and three corresponding outlet channels 810, 812 and 814. Membraneless separator 800 has filters 816 and 818 placed in inlet channels 804 and 808 and has filters 820 and 822 on outlet channels 810 and 814. It will be understood, however, that the invention is not limited by the number of inlet or outlet channels used, nor is the invention limited by requiring each inlet and outlet channel to have a filter. As illustrated in FIG. 8, membraneless separator 800 can be used as a plasmapheresis device. For example, as shown in FIG. 8, plasma from the blood entering extraction channel 802 through inlet channel 806 is skimmed and exits with extraction fluid through outlet channels 810 and 814. This process of skimming is accomplished by withdrawing a greater volume of extraction fluid from outlet channels 810 and 814 than is provided by inlet channels 804 and 808. Thus, this excess volume is removed from the blood fluid. FIG. 8 illustrates a simplification of the layered structure of the flow through the extraction channel 802. In the embodiment illustrated, the sample fluid entering inlet channel 806 and extraction fluid entering inlet channels 804 and 808, and forming layers indicated at 809, undergo progressive change in composition as their contact time increases. As a result, a mixing layer 811 may be characterized where components from both fluids are present in the same proportion. Since there is a tendency for blood cells to migrate toward the low-shear flow centerline of the extraction channel 802, the mixing layer 811 is free of blood cells derived from the sample fluid 806. FIG. 8 illustrates the fact that, at least non-cellular components from the sample layer which enter the mixing layer 811, exit the extraction fluid outlet channel 810. The extraction fluid may include a net gain in volume, thereby, since the mixing layer 811 is shared between the sample fluid outlet channel 812 and each of the two extraction fluid outlet channels 810 and 814.

It should be clear that the illustration of FIG. 8 is figurative and in reality the mixing layer 811 is not distinct with clear boundaries, as depicted. Also, it should be clear from the above discussion and embodiments, that the extraction channel 802 can be used to separate cellular components from blood or to extract cell-free plasma, even in the absence of extraction fluid. The cell-free blood fractions can be effectively skimmed from the layers of the extraction channel fluid which will be relatively free of cells due to the shear-induced self-diffusion of the cells to the center of the flow. This same effect can also be used to concentrate cells in the absence of extraction fluid. The filters (e.g., 822) at the outlets near the walls of the extraction fluid may help to prevent cells from being present in the cell-free fractions taken from the extraction channel 802.

Figure 9:
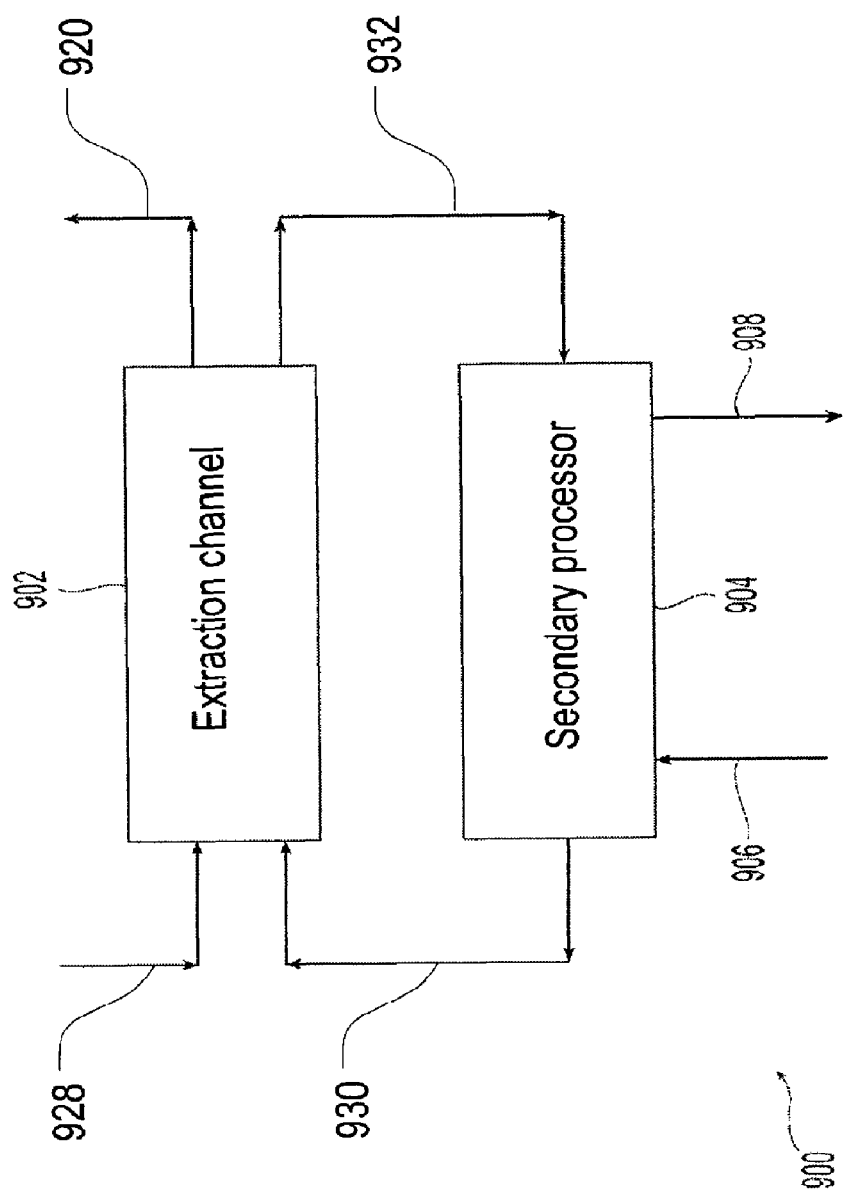
FIG. 9 shows a simplified block diagram of a membraneless separator system including a membraneless separator with filters and a secondary processor.

In preferred embodiment of a renal replacement therapy device, the extraction channel operates in conjunction with a secondary processor that receives extraction fluid from an extraction fluid outlet of the extraction channel, processes the extraction fluid externally of the extraction channel, and returns the extraction fluid to an extraction fluid inlet of the extraction channel. FIG. 9 shows a simplified block diagram of a system 900 including extraction channel 902 and secondary processor 904. Although not shown in detail, it will be understood that extraction channel 902 can have features shown in FIGS. 3 to 8 and described above respect to the various extraction channel embodiments. Blood that is to undergo processing is provided to (and removed from) extraction channel 902 through inlet line 928 and removed through outlet line 920. Meanwhile, extraction fluid that is recycled by secondary processor 904 is also provided to (and removed from) extraction channel 902 by inlet line 930 and outlet 932, respectively. Thus, in this example, there are three fluid streams. The first fluid stream is the blood fluid to be processed carried in inlet and outlet lines 928 and 920. The second fluid stream is the extraction fluid (i.e., extraction fluid or secondary fluid), which contacts the blood fluid in extraction channel 902 and is carried in inlet and outlet lines 930 and 932. The third fluid stream is used to exchange components with the extraction fluid to refresh it and is carried into and out of the secondary processor through inlet and outlet lines 906 and 908, respectively. As also shown in FIG. 9, secondary processor 904 exchanges solutes with the third fluid (e.g., dialysate) across a membrane refreshed by a continuous fresh supply. The third fluid is introduced through inlet line 906 and is output through outlet line 908 after being used by the secondary processor 904. Thus, the extraction channel 902 equilibrates solutes between the sample fluid and the extraction fluid while keeping cells from contacting large area artificial surfaces such as those of a membrane in the secondary processor or the walls of the extraction channel 902.

The secondary processor 904 can use a variety of mechanisms to change the received extraction fluid such that a desired interaction with the sample fluid is achieved. In addition to ultrafiltration, diafiltration, and dialysis, these include sorption, using sorbents targeted to particular small and/or large molecules, chemical reaction, and precipitation. The following international publications describe examples of suitable hemodiafilters: WO 02/062454 (Application No. PCT/US02/03741), WO 02/45813 (Application No. PCT/US01/47211), and WO 02/36246 (Application No. PCT/US01/45369). Moreover, when low-molecular weight solutes are removed by diafiltration in the secondary processor, a stream of sterile buffer is preferably added to the blood to provide a greater volume of fluid, and accompanying small molecules, to pass through the diafiltration membrane in the secondary processor. In conventional diafiltration, such replacement fluid is added before or after the diafilter. In the described embodiment, however, it is advantageous to add it either to the bloodstream or the recycle fluid from secondary processor 904, which is the primary source of extraction fluid.

It will be noted that the secondary processor, working in conjunction with the extraction channel will automatically tend to balance the outflow of macromolecules from the extraction channel against the inflow of macromolecules which have been retained by the secondary processor and conveyed back to the extraction channel. Thus, the secondary processor regulates the operation of the extraction channel through the composition of the recycle stream that it returns to the inlets for extraction fluid of the extraction channel.

In blood therapy, one example of a macromolecule which it is desirable to retain in the blood is serum albumin. In each pass through a diffusion-based exchange device, such as the extraction channel embodiments described, albumin would diffuse at no more than ¼th the rate of small solutes. However, in a renal replacement therapy treatment, a given volume of blood must pass multiple times through the exchange device in order to remove urea from the body because is distributed throughout the total body water compartment. Thus, urea must be picked up from the tissue by a urea-depleted volume of blood and passed to the extraction fluid to be replenished, whereupon the same volume, perhaps ten times in a treatment, returns to the tissues to pick up more urea and deliver it to the extraction fluid. So while albumin diffuses slowly compared to urea, a given molecule of albumin has many more opportunities to be picked up by the extraction fluid. As a result, the fractional removal of albumin, even though its inherent diffusion rate is smaller, may tend to exceed the fractional removal of urea.

The secondary processor (e.g., a membrane device that permits extraction of urea and water but not albumin) can be used to ensure against the removal of albumin to the blood by returning it in the extraction fluid processed by the secondary processor. In contrast, urea is removed from the extraction fluid by the secondary processor and extraction fluid is returned to the extraction channel, depleted of urea. The refreshed extraction fluid is therefore able to pick up more in the extraction channel. As mentioned, the returning stream of extraction fluid may also have a selected water content as well. Thus, the composition of this stream will recruit the further extraction of urea and water but will not recruit further extraction of albumin, given that the difference in albumin concentration between the blood being processed and the extraction fluid will have disappeared.

The difference between the inlet flow rate and the outlet flow rate of the extraction fluid can be controlled to control the compositions of the exiting sample and extraction fluid streams. In the renal replacement therapy embodiments, if the rate of outflow of the extraction fluid from the extraction channel is equal to its rate of inflow, even when urea is removed by the secondary processor, a net flow of albumin and other macromolecules into the outgoing extraction flow will automatically be balanced by a net inflow back into the sample (blood) stream. If there is a higher fluid volume rate of removal from the extraction channel from the rate at which fluid is returned to the extraction channel, the patient's water volume will be reduced by the water draw-down. The concentration in the extraction flow, which is a closed loop, increases until the concentration of macromolecules, including albumin, rises in the recycle stream to match the level in the sample stream such that a transport balance is maintained and no net loss of such components obtains, except for any which may remain in the extracorporeal circuit after treatment is terminated.

When the principal goal of the treatment is the removal of highly diffusible (in general, low molecular weight) molecules, assuming a flow of 20 ml/min flow, the contact area in the extraction channel will be in the range about 17 to 71 cm$^2$. When the principal goal of the treatment is the removal of slowly diffusible molecules (e.g., proteins and especially immunoglobulins), the contact area in the extraction channel will be larger, in the range of approximately 1,700 to 7,100 cm$^2$ (assuming a flow of 20 ml/min), and the secondary processor can be configured to remove these molecules and to recycle smaller molecules (unless their simultaneous removal is desired).

Figure 10:
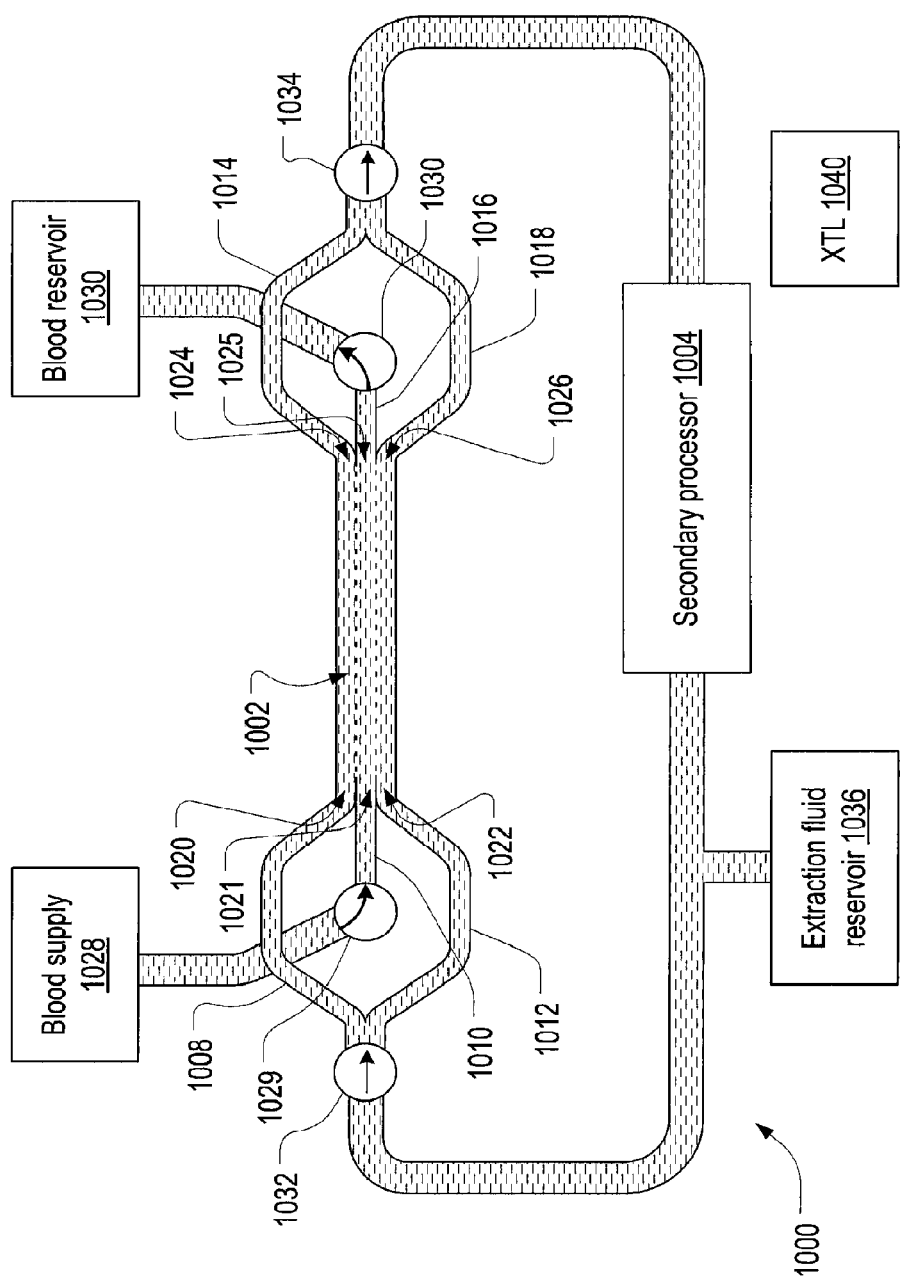
FIG. 10 shows a more detailed view of a system including primary and secondary processors.

A more detailed view of a membraneless separator embodiment, consistent with the embodiment of FIG. 9, is shown in FIG. 10. Blood treatment system 1000 includes an extraction channel 1002 and secondary processor 1004. The extraction channel 1002 has inlet channels 1008, 1010 and 1012 that lead to inlets 1020, 1021, and 1022, respectively. The inlets 1020 and 1022 receive extraction fluid from inlet channels 1008 and 1012, respectively. The inlet 1021 receives sample fluid from inlet channel 1010. The inlets 1020 and 1022 may or may not be filtered as described above. The extraction channel 1002 also has outlets 1024, 1025 and 1026. The outlets 1024 and 1026 receive extraction fluid and convey the same to outlet channels 1014 and 1018, respectively. Sample fluid leaves the extraction channel 1002 through outlet 1025 which conveys the sample fluid to outlet channel 1016. The outlets 1024 and 1026 may or may not be filtered as described above. Preferably, filters are provided and have a pore size of about 100 nm, although the pore sizes could have other sizes as explained above.

System 1000 also includes a blood supply 1028 and a blood reservoir 103 (which, in a treatment setup, would both correspond to a living animal or human patient). A plurality of pumps 1029. 1030, 1032, 1034 are preferably automatically operated. A blood supply 1028 provides blood to extraction channel 1002 through a blood inlet channel 1010. Blood supply 1028 is preferably whole blood from a living animal but can also be an artificial reservoir. Blood withdrawal pump 1030 removes blood from the extraction channel 1002 through blood outlet channel 1016 and conveys it to the blood reservoir 1030, which may be the same as the blood supply 1028 as mentioned. Also, preferably a blood pump 1029, though not necessarily essential, can be provided in line 1010 to pump blood from the blood supply 1028 to the extraction channel 1002.

The flow of extraction fluid into extraction channel 1002, through sheath inlet channels 1008 and 1012 through inlets 1020 and 1022, is controlled by extraction fluid injection pump 1032 (which preferably provides extraction fluid in equal parts to channels 1008 and 1012). The flow of extraction fluid out of extraction channel 1002, through outlets 1024 and 1026 and into outlet channels 1014 and 1018 is controlled by extraction fluid withdrawal pump 1034, which preferably draws equal amounts of extraction fluid out of channels 1014 and 1018. Pump 1034 may be a double pump such as a two-chamber pump or two peristaltic pumps with rotors on a common shaft. Alternatively two separate pumps (not shown) can be use on each of the lines 1014 and 1018 and feedback-controlled to balance the flow through the lines 1014 and 1018 while regulating the total flow of extraction fluid from the extraction channel 1002. Pump 1032 may also be a double pump such as a two-chamber pump or two peristaltic pumps with rotors on a common shaft (not shown). Pump 1032 may be replaced by two separate pumps (not shown) on each of the lines 1008 and 1012 which are feedback-controlled to balance the flow through the lines 1008 and 1012 while regulating the total flow of extraction into the membraneless processor 1002. The use of separate pumps can also provide the ability to convey different fluids, or the same or different fluids at different rates, to inlet channels 1008 and 1012. Thus, the extraction fluid entering inlet channel 1008 can be substantially similar to, or different from, the extraction fluid entering inlet channel 1012. It should be understood that the invention is not limited by the particular types of pumps or flow rates and it should be clear that many variations are possible.

Pumps 1029, 1030, 1032, and 1034 (or other possible pump arrangements) can be used to control the flows of the extraction fluids and blood fluid so as to withdraw only the extraction fluids or the extraction fluids plus a prescribed amount of blood fluid through filters 1024 and 1026. Likewise, pumps 1030, 1032, and 1034, and if present, pump 1029, can be controlled to regulate the flows of the extraction fluids and blood fluid to regulate the contact between the cell-containing sample layer and filters 1020 and 1022. In a preferred configuration, the control is such that water volume to be drawn down from a patient is performed at as low a rate as possible and therefore that the net draw-down be accomplished over a maximum duration consistent with the desired treatment time and patient requirements. The water drawdown is accomplished by drawing a larger volume through the outlet channels 1014 and 1018 than replaced through the inlet channels 1008 and 1012. Thus, the pumps are preferably controlled to minimize the difference in outlet and inlet flow rates and to regulate the two rates precisely. In addition, the outlet flow rates through line 1014 and line 1018 are preferably kept precisely the same to avoid sucking the cell-containing layer through one of the extraction fluid outlet lines 1014 and 1018 as a result of an imbalance. By precisely regulating the mean and instantaneous flow rates, the interface between the center cell-containing layer and the fluid outlets 1025 can be maintained to ensure that a minimum of blood cells contact the extraction channel 1002 walls or the filters 1024 and 1026, which is preferred.

System 1000 can also include an extraction fluid reservoir 1036. Extraction fluid reservoir 1036 provides a supply of fresh extraction fluid (e.g. such as replacement fluid used in hemofiltration or dialysate for preferred blood treatment embodiments) to the flow loop between extraction channel 1002 and secondary processor 1004. Under normal operation of some embodiments, components of the blood fluid that have diffused into the extraction fluid are removed by secondary processor 1004. Under certain conditions, blood cells or other blood fluid components, such as fibrinogen, that diffuse into the extraction fluid from the blood fluid may collect along the surface of outlet filters 1024 and 1026. These materials can be removed from the surfaces of filters 1024 and 1026 by temporarily reversing the flow of the extraction fluid to flush the filters 1024 and 1026 using only a small quantity of extraction fluid. This amount of extraction fluid can be replenished from extraction fluid reservoir 1036 upon reestablishing normal co-current flow of extraction fluid relative to the blood fluid. The need to perform this "blowback" operation can be determined by pressure drop across the filters or flow measuring devices. These devices can be integrated into system 1000. The extraction fluid reservoir can also serve as a source of replacement fluid for treatments, where more water and solute volume are deliberately eliminated in the secondary processor than are to be eliminated from the patient for treatment purposes, as is done in hemofiltration, for example. The pumps may be automatically controlled by a controller 1040, which preferably includes a programmable processor.

Preferably, in blood treatment embodiments, the extraction fluid provided to extraction channel 1002 (from separator 1004 and/or optional extraction fluid reservoir 1036) by extraction fluid injection pump 1032 occupies approximately $2/3$ of the cross-section of extraction channel 1002, with blood from blood supply 1028 in the middle $1/3$. (This flow configuration is illustrated in FIG. 1A.) This configuration can be maintained by appropriately regulating the inflow of blood and extraction fluid. In this configuration, each half of the blood layer in extraction channel 1002 is "serviced" by one of the sheathing layers, and the sheathing layers are traveling at an average velocity that is approximately half that of the blood, though the interfacial velocities of the blood and extraction fluids are approximately equal. Thus, the volume of blood and the volume of extraction fluid that pass through the unit in a given period of time are approximately equal. Although the invention is not limited in this manner, it should be noted that, in the configurations described here, the exchange efficiency drops, from the maximum of 50% associated with equilibrium, when the volumetric flows of the two fluids (e.g., blood and extraction fluid) are different from each other.

In order to cause the separation (or skimming) of all or part of the cell-free component of the blood being processed, the inlet and exit flows of the extraction fluid may be controlled (via pumps 1032 and 1034, respectively) such that more total fluid is withdrawn from extraction channel 1002 through outlet channels 1014 and 1018 than extraction fluid provided through inlet channels 1008 and 1012. Thus, a portion of the blood being processed is removed along with the extraction fluid through outlet channels 1014 and 1018. For example, it is possible to skim 10% of the blood flow by running extraction fluid withdrawal pump 1034 at a rate that is 10% higher than the rate of extraction fluid injection pump 1032. It will be appreciated that, when this is done, the blood efflux rate is determined and need not be controlled, as it should naturally have an outflow that is 90% of the inflow.

As explained above, when indiscriminate plasma removal is not desired, the plasma that is skimmed from the blood using extraction channel 1002 is processed by secondary processor 1004, which regulates the operation of the extraction channel 1002 through the flow rate and composition of the recycle stream that it returns to sheath inlet channels 1008 and 1012 (i.e., a recycle stream is used to limit transport of blood components for which extraction is not desirable). A substantial benefit arises because secondary processor 1004 is able to achieve high filtration velocities due to the fact that concentration polarization is limited to proteins and does not involve cells. Moreover, because cells are retained in extraction channel 1002, though the action of cell migration (described below), supplemented by the action of the filters, a majority of these cells would see artificial material only on its conduit surfaces. While some relatively small amount of cells may contact the filters 1024 and 1026 in outlet channels 1014 and 1018, the contact is limited to a small fraction of the total number of cells and occurs for a relatively short time. Because cell contact on the liquid-liquid contact area is far less traumatic, mechanically and chemically, a reduction in bio-incompatibilities and a reduced (or eliminated) need for anti-coagulation is achieved. Additionally, because the primary transport surface in the system is intrinsically non-fouling and the surface of the filters is swept clean by the fluid shear rate, a major deterrent to long-term or continuous operation is removed, opening the possibility of a wearable system with the recognized benefits of prolonged, slow exchange.

It should be understood that operation of extraction channel 1002 that allows the sheath exit flows to be larger than the corresponding inlet values will induce a convective flow from the blood stream, over and above the diffusive flow. In order to prevent such a convective flow from carrying blood cells with it (as would be the case if the distribution of cells in the blood stream was uniform), it is important that cellular components of the blood have migrated to the center of the blood stream in order to permit significant plasma skimming. Centripetal drift of cells occurs under a variety of flow regimes in the disclosed embodiments. The flow conditions can be adjusted to cause blood cells to move away from the blood-liquid interface. For example, when blood flows in a tube below a wall shear rate (measured as the blood-flow velocity gradient perpendicular to the tube wall) of about 100 reciprocal seconds, this shear rate causes cellular components to migrate to the center of the tube. Thus, the occurrence of cell contact with the filters is reduced. (See Goldsmith, H. L. and Spain, S., Margination of leukocytes in blood flow through small tubes, Microvasc. Res. 1984 March; 27(2):204-22.).

It will be appreciated that long-term stability is necessary for satisfactory operation of the microfluidic devices described herein. For example, it is desirable to prevent inappropriate differences in sheath inlet and outlet channel flows, which, uncorrected, could result in unintended infusion of sheathing solution into the bloodstream. Accordingly, on-board electronics and photonics (not shown), which are common features of chip-based microfluidic devices, can be used to regulate system 1000 (e.g., to introduce flow changes) with an electrically activated device (e.g., a piezoelectric valve) that is mounted on the same plate, or "chip," on which extraction channel 1002 is located.

An ultramicroscope (or other device that is sensitive to the presence of dilute particles) can be used to monitor the fluid exit stream in the extraction fluid outlet channels 1014 and 1018 for the presence of cells in the extraction fluid, as might occur on failure of one of filters 1024 and/or 1026 on the outlet channels. Additionally, controls are preferably provided to protect against flow imbalances that might cause blood losses or hypervolemia, which are naturally prevented when a membrane is present but which may occur in a membraneless device. For example, a control system may be provided which shuts down the system and initiates an alarm when cells are detected in the extraction fluid outside the membraneless processor or when independent flow measuring sensors detect a flow imbalance between blood and net sheath flow beyond a threshold imbalance, which might obtain when a prescribed quantity of plasma is removed or when hypervolemia is being treated.

As explained above, in the extraction channel, the fluids (e.g., blood and extraction fluid) preferably flow in the same direction. In particular, flow in opposite directions tends to disrupt the blood-fluid interface and induce undesirable mixing. When fluids flow in the same direction, the greatest exchange rate that can be achieved obtains when equal volumes of fluids the sheath and blood streams achieve equilibrium (which, according to Loschmidt's formula provided above, means that if the extraction fluid flows at the same rate as blood, the extraction E of a solute cannot exceed ½). In other words, if the two flows are equal, at most half of the solute can be transferred. Moreover, while greater flows permit larger fractions, E, of a solute to be removed, they require higher circulation rates to the secondary processor and thus force processing of solutes at lower concentrations, which is generally undesirable. Therefore, it is generally desirable for these flows to be nearly equal, or at least within a factor 3. Of course, this description applies where the sample and extraction fluids have similar properties, such as their capacity to store solutes and/or other exchanged components, and the proportions can be adjusted accordingly when fluids with differing properties are used.

Figure 11:
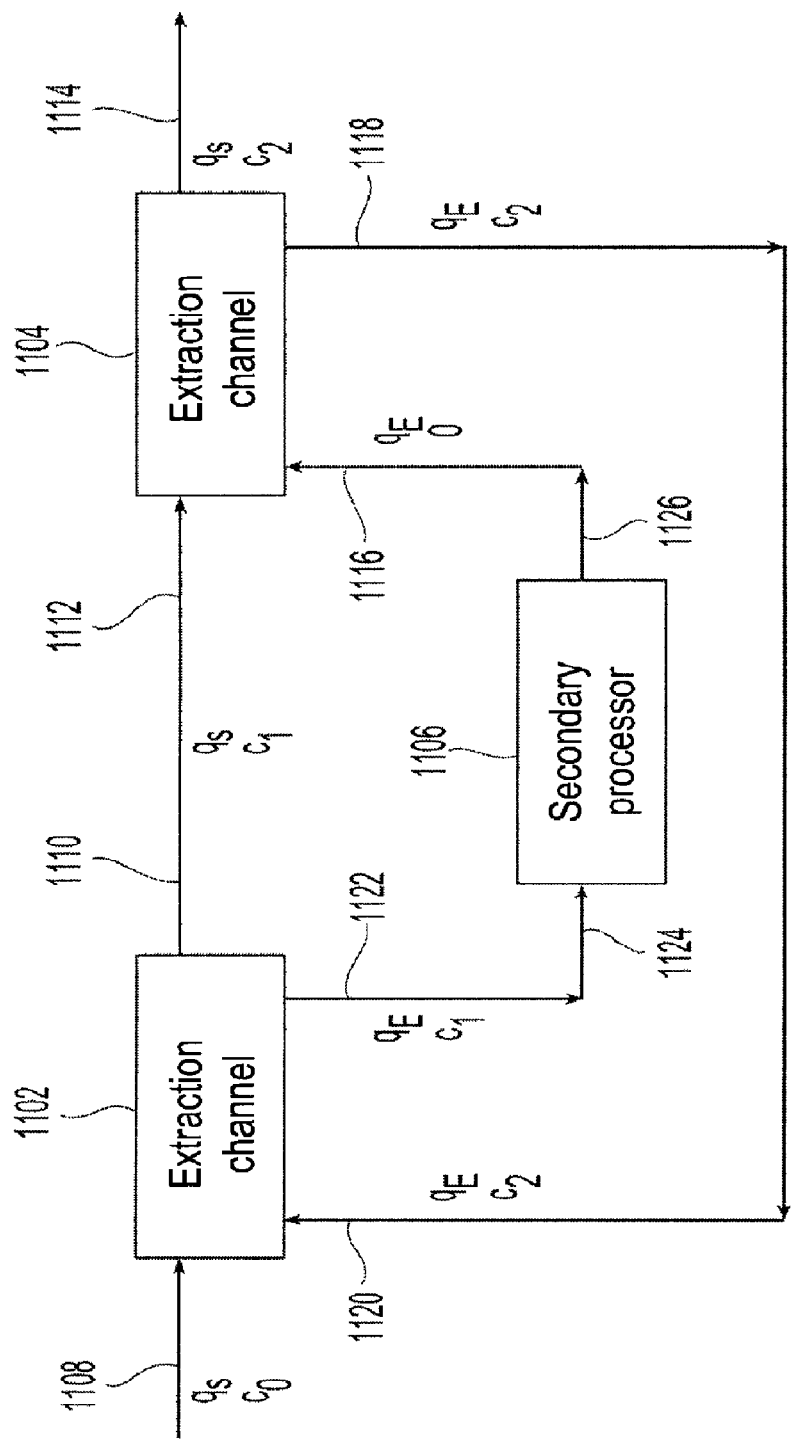
FIG. 11 shows the configuration of a system subdivided into two units, arranged to achieve a pseudo-countercurrent flow of sample and extraction fluids.

This limitation on extraction efficiency can be overcome by a configuration shown in FIG. 11 and described below which achieves the effect of opposing flows (counterflow) by the interconnection of more than one concurrent membraneless processor. In particular, low extraction efficiency can be overcome by more sophisticated layouts of a microfluidic system such that flows are concurrent in each unit of the system, but the overall flow approaches countercurrency in pattern and efficiency.

Subdivision of a given desired contact area into n units (stages) each connected to the other in a countercurrent manner is used to allow extraction efficiency to rise above 50%. Although FIG. 11 shows an example of a two-stage membraneless separation system, other embodiments can have more than two stages. Each addition stage results in an increase in extraction. Referring to FIG. 11, a two-stage membraneless separation system 1100 has a first stage extraction channel 1102 and a second stage extraction channel 1104. The system 1100 also includes a secondary processor 1106, also described above, for removing components from the extraction fluid between the two stages 1102 and 1104. A sample fluid is fed into a sample inlet 1108 of the first stage extraction channel 1102 at a sample fluid flow rate of $q_S$, having a concentration of a given component of $c_0$. The sample fluid exits first stage extraction channel 1102 through a sample outlet 1110 and enters a sample inlet 1112 of second stage extraction channel 1104 at a concentration of $c_1$. The flow of sample fluid is assumed to be approximately equal throughout both stages. Finally, the sample fluid exits second stage extraction channel 1104 by a sample outlet 1114 at a concentration of $c_2$.

A clean extraction fluid is fed into an extractor inlet 1116 of second stage extraction channel 1104 at an extraction fluid flow rate $q_E$ the flow of extraction fluid is assumed to be approximately equal throughout both stages. Because the extraction fluid is clean, the concentration of the given component will be assigned a value of zero. The extraction fluid exits second stage extraction channel 1104 through an extractor outlet 1118 and enters first stage extraction channel 1102 through an extractor inlet 1120. If sufficient contact area between the sample fluid and extraction fluids is maintained in each extraction channel stage 1102 and 1104 for a sufficient time, as determined by the calculations above, the concentration of the given component will approach equilibrium between the sample fluid and the extraction fluids. Thus, the concentration of the extraction fluid leaving extractor outlet 1118 of second stage extraction channel 1104 is assumed to be equal to $c_2$. The extraction fluid exits first stage extraction channel 1102 by an extractor outlet 1122 and is returned to secondary processor 1106 through an extractor inlet 1124. As with second stage extraction channel 1104, the concentration of extraction fluid exiting outlet 1122 is assumed nearly equal to the concentration of the exiting sample fluid. Thus, the concentration of the extraction fluid is $c_1$. The components collected by the extraction fluid are removed in secondary processor 1106 so that clean extraction fluid exits secondary processor 1106 by an extractor outlet 1126 and can be recirculated to extractor inlet 1116 of second stage extraction channel 1104. Mass balance calculations may be performed for each stage of the two-stage membraneless separation system 1100 in order to find the fractional clearance $Cl/q_S$ of the given component. Using the concentration and fluid flow variables defined above, the first stage extraction channel 1102 mass balance can be written as $q_S c_0 + q_E c_2 = (q_S + q_E) \cdot c_1$. The second stage extraction channel 1104 mass balance can be written as $q_S c_1 + q_E 0 = (q_S + q_E) \cdot c_2$ where $c_0 = 1$, and the fractional clearance $Cl/q_S$ is equal to $1-c_2$, and the relationship between the fractional clearance and extraction/sample fluid flow ratio is $$\frac{Cl}{q_S} = \frac{\lambda^2 + \lambda}{\lambda^2 + \lambda + 1}.$$

Thus, Cl approaches the value of the sample fluid flow as approaches infinity. When the extraction fluid flow total is twice that of the sample fluid flow (i.e. $\lambda=2$), the fractional clearance is approximately 0.86. In contrast, in a non-staged, single pass membraneless separation system, the best efficiency is equilibration of each half of the sample fluid with the corresponding extraction fluid in contact with that half of the sample fluid. Therefore, the two-stage extraction channel system 1100 is more efficient than the single-pass system at removing components from the sample fluid at equal extraction fluid flow rates. While two stages are shown in FIG. 11, any number of stages (e.g., 3, 4, 5, or more) can be used in system 1100, all of which can be easily provided on a single substrate or set of substrates, fabricated according to known techniques for the fabrication of microfluidic devices. Thus, in a preferred embodiment, the multiple stages can be provided without introducing any external connections between microfluidic stages.

In a preferred embodiment, each of the extraction channels has filters, of the type described with regard to FIGS. 3-8, in the extraction fluid outlets 1122 and 1118. In one embodiment, only the extraction fluid outlet 1122 that is connected to the secondary processor 1106 is filtered.

The devices, systems and methods disclosed, with the appropriate selection of filter pore size, are capable of diffusing various blood components having different sizes, including 'small molecules, 'middle' molecules, macromolecules, macromolecular aggregates, and cells, from a blood sample to the extraction fluid. This ability is particularly important considering the fact that different treatments require the removal of different sized particles. For example, in dialysis, one may desire to remove molecules of low molecular weight, while in the treatment of acute liver failure, both small and intermediate-sized molecules are to be removed. In therapeutic apheresis, meanwhile, one generally wishes to remove selected protein macromolecules (e.g., immunoglobulins), while in the treatments for fulminating sepsis, it is toxins of intermediate molecular weight that one generally desires to remove. On the other hand, in proposed anti-viral treatments, one wishes to remove free viral particles, while in the treatment of congestive heart failure, one simply wishes to remove water and a non-selective cohort of electrolytes.

The treatment to which extraction fluid is subjected in the secondary processor may be substantially the same as those performed in the various types of conventional treatment using whole blood or cell-free plasma. A secondary processor can include any of a variety of devices used for refreshing the extraction fluid. For example, a membrane device or a sorption device could be used. In addition, the extraction channel and secondary processor system is not limited to application to renal replacement therapy. For example, such a system can also used to remove, destroy or inactivate a substance related to a specific disease. Examples include enzyme reactors, cryoprecipitators, and/or ultraviolet irradiators. The system can also be used for extracting components from a non-blood sample fluid, in which a secondary processor receives the extraction fluid and at least some of the components of the sample fluid which are not to be removed.

Note that although in the foregoing and following discussions, although a single extraction channel and a single secondary processor may be identified, it is assumed that the singular nouns do not necessarily refer to a single component. For example, multiple extraction channels may be formed in a layered or folded structure to achieve compactness with high contact area between sample and extraction fluids.

The interface between the first extraction fluid and the sample fluid, within the extraction channel, can be varied by adjusting the relative flow rates of the first extraction fluid and the sample fluid. Additionally, a detector may be placed in the outlet receiving stream or streams to detect substances in the exiting fluid(s), for example, undesirable blood components in the exiting extraction fluid or within the extraction channel. A signal from the detector may then be used to adjust the relative flow rates of sample and extraction fluids. An example of a detector is an opacity monitor or ultramicroscope in the extraction channel which can detect erythrocytes in the extraction channel outlet which should receive non-cellular fluid. Another example of a detector is a hemoglobin detector which may indicate the rupture of blood cells due to improper fluid flows. Total and relative extraction and sample fluid flow rates can also be adjusted to correct such a condition.

A method is described for selectively extracting components from a sample fluid includes providing a microfluidic extraction channel having at least a first inside surface and a second inside surface and establishing laminar flows of a first extraction fluid, second extraction fluid, and sample fluid within the microfluidic extraction channel. The laminar flow of the first extraction fluid within the extraction channel is in contact with the first inside surface of the extraction channel, and the laminar flow of the second extraction fluid within the extraction channel is in contact with the second inside surface of the extraction channel. The laminar flow of the sample fluid is disposed between and in contact with the first and second extraction fluids within the extraction channel. The first extraction fluid and a first portion of the components of the sample fluid are withdrawn from the extraction channel through a first filter, the first filter having pores sized to exclude components larger than a first size. Likewise, the second extraction fluid and a second portion of the components of the sample fluid are withdrawn from the extraction channel through a second filter, the second filter having pores sized to exclude components larger than a second size. The remaining sample fluid is withdrawn from the extraction channel.

As mentioned above, the embodiments described herein allow the purification of blood without the use of a membrane by contact of the blood with a miscible fluid under conditions that prevent turbulent mixing. It is appreciated that embodiments described herein are useful in hemodialysis, for example. However, it should also be noted that the embodiments, and variations thereof, are also useful in other situations where exchange between a sample fluid and another fluid is desired via a diffusion mechanism.

The interface area provided by the extraction channel for a specified exchange rate can be achieved by appropriate combinations of channel length, width, and number according to the principles described herein. The required area can be obtained by providing multiple extraction channels and by providing a sheathing flow so that each channel contains two interfaces. It is shown herein that the competing requirements of small height (to avoid excessive diffusion times and in-process volumes), short length (to avoid excessive pressure drop) and practical limitations on width of a single device, which suggests the need to array them in parallel, side-by-side or in a stack can be satisfied in practical microfluidic devices.

The described embodiments can be used to process the blood of a single individual for the purpose of treating a large number of disease conditions. For example, therapies described above can be used in the treatment of acute renal failure, acute liver failure, high antibody levels in myasthenia gravis and other autoimmune diseases. Additional uses include, for example, the removal by either precipitation or sorption of LDL in homozygous hyperlipidemia, in addition to the removal of malignant sepsis or fluid in cases of congestive heart failure, for example. The described embodiments can also be used to aid in the reduction of viral burdens in AIDS patients, as well as for treatment of patients requiring other types of blood purification. Patients with diabetes, patients that have suffered a drug overdose, patients that have ingested a poison, patients suffering from renal failure, patients suffering from acute or chronic liver failure, or patients that have Myasthenia gravis, lupus erythematosis, or another autoimmune disease can also benefit from the devices and systems described above. For example, while an exchange device according to the invention is not a cure for diabetes, it can be useful in the amelioration one or more symptoms of diabetes. Moreover, the embodiment described above could be useful in clearing the blood of IgG molecules or other molecules, which are causative of an autoimmunity disorder. Additionally, embodiments according to the invention can be used in acute dialysis or for extended dialysis. Patients (or animals, in the case of veterinary use) suffering from disorders, diseases and syndromes not listed herein can also be treated.

The membraneless devices and systems described are preferably embodied in systems that provide extended treatment times, low extracorporeal blood volume, it is therefore possible to provide them in a compact configuration. In one embodiment, a wearable (or at least portable) system according to the invention can run between 20 and 24 hours per day at a flow rate of about 20 cc/min, for example. The patient could then have, for example, 4-5 hours each day without the device in place which could be used for personal hygiene (e.g., showers or baths), sports activities, or other activities not amenable to the small system being worn or used. The embodiment described above thus addresses a problem recognized by the dialysis community (e.g., the negative side effects such as physical exhaustion, thirst, etc. associated with an episodic dialysis schedule), for which daily or nocturnal hemodialysis is not always a sufficient alternative. In particular, the embodiment described herein allows the patient to move about in a normal manner (e.g., go to work, school, home, etc.) while being subject to ongoing dialysis.

In addition to the treatment of various disease states, a device or system according to the invention can also be used for extracting blood components that are useful in treating others, as well as for purposes of studying the processes by which molecules and cells segregate and diffuse in blood. For example, diffusion of individual molecular species in blood may not occur independently and may not depend on size in the simple manner dictated by the Stokes-Einstein equation. Moreover, many solutes may partition into multiple forms: free, in complexes, bound to plasma protein, bound to cell-surface moieties, or as intracellular solutes. Relative to the rate of diffusion of the solute, its different forms may or may not be in local equilibrium. These phenomena are likely obscured when a membrane is present because it slows and controls overall transfer rates. Therefore, a membraneless device or system according to the invention can be a useful scientific tool to study these phenomena and a system in which rates are raised enough that partitioning may set limits on how much and how quickly a solute can be removed. A particular example is bilirubin bound to albumin. Another example is inorganic phosphorous which exists as partially ionized salts, as two anionic forms in plasma and in several intracellular forms.

Although the present specification is primarily concerned with blood treatment for end stage renal disease, extraction of blood components can be used to remove other components for treatment, such as free viral particles and, in the treatment of congestive heart failure, to remove water and a non-selective cohort of electrolytes. Additional uses for extracorporeal processing include extracting blood components useful in either treating others or in research. Apheresis of plasma (i.e., plasmapheresis) and thrombocytes, or platelets, is the procedure most commonly employed for this purpose. Although the present specification discusses primarily blood processing and issues related thereto, many of the methods discussed may be used for processing other fluids as well, such as blood components.

Also, the extraction channel and associated elements discussed herein may be used in a secondary processor and may be chained to form multiple stages to select fluid components. For example, a chain of two extraction channels would convey the extraction fluid of a first extraction channel to the sample fluid path of a second extraction channel, thus forming a cascade. The second extractor may have, for example, filters in its walls with pore sizes that are smaller than those of the first such that the sample fluid from the second extraction channel contains intermediate sized particles, but a reduced fraction of the smallest particles. Such a cascade may include an arbitrary number of stages.

Persons skilled in the art will also appreciate that the present invention can be practiced by other than the described embodiments, which are presented for purposes of illustration and not of limitation, and that the present invention is limited only by the claims that follow.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of performing ultrafiltration, comprising:
    pumping blood from a human patient into a microfluidic channel to generate a shear flow across the face of filters forming opposite facing walls of the microfluidic channel, the shear flow in the microfluidic channel being maintained at a sufficient magnitude to prevent the clogging of the filters;
    drawing plasma through the filters and removing water and uremic toxins from the plasma by passing the same through an ultrafilter at a higher shear rate than would be tolerated by blood due to the concomitant rate of hemolysis; and
    returning dehydrated plasma to the patient.

2. The method of claim 1, wherein the ultrafilter is a microfiber bundle type dialyzer.

3. The method of claim 1, wherein the microfluidic channel has a depth across the direction of blood therethrough of 300 microns or less.

4. The method of claim 1, wherein the microfluidic channel has a depth across the direction of blood therethrough of about 100 microns.

5. The method of claim 1, wherein the width of the microfluidic channel across the direction of flow is at least ten times the depth.

6. The method of claim 1, wherein each of the filters forming opposite facing walls has an array of holes that are less than 800 nm.

7. The method of claim 1, wherein each of the filters forming opposite facing walls has a regular array of holes that are less than 800 nm.

8. The method of claim 1, further comprising pumping the plasma, the pumping controlling a rate of the drawing.

* * * * *

UNITED STATES PATENT AND TRADEMARK OFFICE
CERTIFICATE OF CORRECTION

PATENT NO. : 8,257,593 B2  
APPLICATION NO. : 13/332040  
DATED : September 4, 2012  
INVENTOR(S) : Edward L. Leonard et al.

Page 1 of 1

It is certified that error appears in the above-identified patent and that said Letters Patent is hereby corrected as shown below:

On the Title page of the patent, please add the following underlined section under the heading "Related U.S. Application Data":

Related U.S. Application Data

(60) Continuation of application No. 12/759,157, filed on Apr. 13, 2010, now Pat. No. 8,097,153, which is a division of application No. 11/814,117, filed as application No. PCT/US2007/069414 on May 22, 2007, now Pat. No. 7,727,399.
(60) Provisional application No. 60/802,471, filed on May 22, 2006.

Signed and Sealed this
First Day of January, 2013

David J. Kappos
*Director of the United States Patent and Trademark Office*